United States Patent
Ludwick et al.

(10) Patent No.: US 8,196,479 B2
(45) Date of Patent: Jun. 12, 2012

(54) PORTABLE MULTI-TUBE AIR SAMPLER UNIT

(75) Inventors: Richard K. Ludwick, Overland Park, KS (US); Keith D. Wilson, Lee's Summit, MO (US)

(73) Assignee: Midwest Research Institute, Inc., Kansas City, MO (US)

( * ) Notice: Subject to any disclaimer, the term of this patent is extended or adjusted under 35 U.S.C. 154(b) by 425 days.

(21) Appl. No.: 12/582,038

(22) Filed: Oct. 20, 2009

(65) Prior Publication Data

US 2011/0088490 A1    Apr. 21, 2011

(51) Int. Cl.
G01N 1/24 (2006.01)
G01N 1/34 (2006.01)
G01N 1/40 (2006.01)
G01N 1/44 (2006.01)
G01N 30/20 (2006.01)

(52) U.S. Cl. ........... 73/863.31; 73/23.41; 73/31.02; 73/31.07; 73/863.01; 73/863.02; 73/863.11; 73/863.12; 73/863.21; 73/863.23; 73/863.25; 73/863.33; 73/86.71; 73/864.34

(58) Field of Classification Search ........... 73/23.37, 73/23.41–23.42, 28.01, 28.04, 31.02, 31.07, 73/863.01–863.02, 863.11–863.21, 863.23, 73/863.25–863.31, 863.33, 863.71, 864.34, 73/864.81, 864.83, 864.85
See application file for complete search history.

(56) References Cited

U.S. PATENT DOCUMENTS

| | | | |
|---|---|---|---|
| 3,369,405 A * | 2/1968 | Galegar | 73/863.21 |
| 3,474,659 A * | 10/1969 | Kelleher | 73/863.31 X |
| 3,731,539 A * | 5/1973 | Brittan et al. | 73/863.11 |
| 3,903,745 A | 9/1975 | Bolser | |
| 4,090,392 A * | 5/1978 | Smith et al. | 73/863.23 |

(Continued)

FOREIGN PATENT DOCUMENTS

EP    185926 A * 7/1986
(Continued)

OTHER PUBLICATIONS

Bioenvironmmental Engineering Strategic Planning Session; Detection Equipment Program: Live Agent Testing; Robert B. Walton, Maj PhD CIH, U.S. Air Force, 2003-2004, Slides 1, 27, 49 and 60 of 61, downloaded Mar. 23, 2012, Slide 1 at http://www.aiha.org/aihce04/handouts/rt205walton_files/frame.htm#slide0017.htm.*

*Primary Examiner* — Thomas P Noland
(74) *Attorney, Agent, or Firm* — Samuel Digirolamo; Husch Blackwell LLP

(57) ABSTRACT

A portable multi-tube air sampler device for capturing samples of trace elements in a suspected contaminated environment which includes a plurality of sample tubes for collecting sample trace elements, parallel inlet and outlet manifolds which minimize the length of the sample inlet path while utilizing short straight sample tubes, a hinged retainer bar mechanism which allows for easy removal and replacement of the various sample tubes, and a removably attachable controller unit which can be installed on the exterior portion of the carrying case for controlling the operation of the sampling protocol. Other embodiments include heated inlet manifold and sample intake paths to prevent contamination accumulation and carryover, a clean cycle option with a filter valved into the inlet flow path to enhance the purging cycle, and a mechanism for converting the present device to a desorbing auto sampler configuration. The present system likewise incorporates a purging cycle prior to each sampling cycle.

50 Claims, 11 Drawing Sheets

U.S. PATENT DOCUMENTS

| | | | |
|---|---|---|---|
| 4,324,146 A | | 4/1982 | Born |
| 4,584,887 A | | 4/1986 | Galen |
| 4,704,910 A | * | 11/1987 | Conrad ........................ 73/863.21 |
| 4,779,466 A | * | 10/1988 | Ramsner et al. ............ 73/863.33 |
| 4,786,472 A | | 11/1988 | McConnell et al. |
| 4,883,505 A | | 11/1989 | Lucero |
| 4,993,271 A | * | 2/1991 | Vargason ............... 73/863.33 X |
| 5,162,652 A | * | 11/1992 | Cohen et al. ............ 73/863.33 X |
| 5,319,986 A | | 6/1994 | Padden et al. |
| 5,321,984 A | * | 6/1994 | Stroupe ....................... 73/863.11 |
| 5,333,511 A | | 8/1994 | Boyum et al. |
| 5,404,763 A | * | 4/1995 | Guggenheim ............ 73/863.31 |
| 6,167,767 B1 | | 1/2001 | Mengel et al. |
| 6,244,117 B1 | | 6/2001 | Mengel et al. |
| 6,272,937 B1 | | 8/2001 | Mengel et al. |
| 6,321,609 B1 | | 11/2001 | Mengel et al. |
| 6,477,906 B1 | | 11/2002 | Peterson |
| 7,430,893 B2 | | 10/2008 | Grayfer et al. |
| 7,569,093 B2 | * | 8/2009 | Pranda et al. .......... 73/863.31 X |
| 2005/0170520 A1 | | 8/2005 | Schur et al. |
| 2006/0093523 A1 | | 5/2006 | Norman |
| 2007/0068284 A1 | | 3/2007 | Castro et al. |
| 2007/0107495 A1 | | 5/2007 | Kim et al. |
| 2007/0107537 A1 | | 5/2007 | Bell et al. |
| 2007/0107538 A1 | | 5/2007 | Bell et al. |
| 2008/0135236 A1 | * | 6/2008 | Schoell ....................... 166/250.1 |
| 2008/0202206 A1 | * | 8/2008 | Nelson et al. .......... 73/863.21 X |
| 2008/0229805 A1 | | 9/2008 | Barket et al. |

FOREIGN PATENT DOCUMENTS

| | | | | |
|---|---|---|---|---|
| EP | 476674 A1 | * | 3/1992 | ................ 73/863.01 |
| EP | 971211 A2 | * | 1/2000 | |
| GB | 1450262 A | * | 9/1976 | |
| WO | WO 9217762 A1 | | 10/1992 | |
| WO | WO 9521382 A2 | * | 8/1995 | |

* cited by examiner

PORTABLE MULTI-TUBE AIR SAMPLER UNIT

BACKGROUND OF INVENTION

The present invention relates generally to air sampling devices used for gathering and analyzing trace elements from a particular environment such as a suspected contaminated area and, more particularly, to several embodiments of a lightweight, portable multi-tube sampler device capable of acquiring multiple samples of trace elements such as concentrations of chemical agents and toxic industrial chemicals for subsequent analysis by a mass spectrometer or other analyzing unit at a remote location.

There are many applications in which it is desirable to collect and capture air samples from a particular environment suspected of contamination such as collecting air samples in potential hazardous chemical release situations, collecting vapor samples from bulk chemical storage locations, and/or collecting air samples in potential chemical agent release situations. Many different types of sampling devices exist today for capturing samples of trace elements or contaminants from a particular environment and, once collected, such samples are analyzed to determine the nature of the chemicals involved, the level of contamination in the air, and the degree of risk personnel may be exposed to in the contaminated area. Some of the known devices utilize a single concentrator tube to acquire samples for trace analysis, while others include multiple concentrator tubes or capture traps for collecting such contaminants. In addition, some known devices provide for immediate analysis whereas others allow the concentrator tubes to be removed for analysis at a remote location.

There are also known existing portable sampling devices for use in the field. One such example of an automatic multi-sorbent tube air sampler is disclosed in U.S. Pat. No. 6,477,906. This sampling system includes a plurality of tubes connected to a single multi-port valve wherein each tube is connected through the valve by means of pairs of valve ports, the inlet and outlet ports of each respective tube being positioned in adjacent ports associated with the multi-port valve resulting in a multi-tube design. The multi-port valve is constructed and operated in a predetermined sequence to create a flow path through the multi-port valve wherein the flow path directs an air sample to only one tube at a given time. The multi-port valve also includes a plurality of park positions between the respective ports wherein the valve can be set in a corresponding park position between ports thereby isolating all tubes in this position from the flow path while at the same time requiring minimum movement of the valve to the next operative position for the next tube when a sample is to be taken. In addition, each sample tube is mounted on coiled tubing springs so that a sample tube can be desorbed and analyzed while the sample tube remains coupled to the sampling device. This system also permits cleaning, sampling and desorption of the sample tubes without removing the sample tubes from the system. Because of its construction, only one sample tube can be desorbed at a time; no additional sample tubes are provided in the overall unit; the individual sample tubes are not easily replaced; and the entire unit cannot be placed back in service until all of the individual tubes are desorbed and analyzed.

Another existing unit in the field is the HAPSITE field portable mass spectrometer unit which uses a single collector tube to acquire samples for trace analysis. In the field, sampling/analysis turnaround time and battery power limit the user of this device to acquiring only 7 or 8 samples total per battery charge. Also, importantly, since the HAPSITE device includes only a single concentrator tube, only one sample at a time can be taken. Once a sample is taken, the HAPSITE sample must be analyzed before the single concentrator tube can be cleaned and desorbed for taking another sample. In addition, the HAPSITE unit's bulk and the necessity to analyze the samples on site limit the user's mobility and prolongs the exposure of field personnel to potentially hazardous environments.

It is therefore desirable to provide a portable multi-tube air sampling unit which is capable of acquiring multiple samples using an improved manifold design which minimizes the length of the sample path and which includes a hinged retainer bar mechanism which allows for relatively quick and easy removal and replacement of the various sample tubes so that more samples can be collected without waiting for the first batch of samples to be analyzed. This will allow the sampling unit to return to the field while the contaminants collected in the previous batch of tubes are still being analyzed at a remote location.

It is also desirable to provide a portable multi-tube air sampler unit which includes a removable plug-in controller device which can be installed on the outside of the unit for controlling the operation of the sampling protocol. It is also desirable to provide a unit wherein the sample acquisition times can be reduced so as to minimize exposure of field personnel to potentially hazardous situations.

Accordingly, the present invention is directed to a portable multi-tube air sampling device which overcomes one or more of the problems set forth above.

SUMMARY OF INVENTION

The present invention overcomes many of the shortcomings and limitations of the prior art devices discussed above and teaches the construction and operation of several embodiments of a portable multi-tube air sampler device adaptable for use in a wide variety of different applications including using sampling tubes adaptable for attachment to different types of analyzing units such as a HAPSITE device.

The present device is a lightweight portable battery-operated unit that can hold a plurality of sample/concentrator tubes such as, for example, seven tri-bed concentrator tubes and one type 5 cartridge tube. The present device is capable of collecting multiple samples for analysis and, in one embodiment, the sample tubes are specifically designed to work with and attach to a HAPSITE analyzer. In this particular embodiment, once a plurality of samples have been taken in any number of the tubes associated with the present device, at least some of the tubes can be individually removed and attached to a HAPSITE device for analyzing the sample. It is recognized and anticipated that the individual sample tubes associated with the present invention can likewise be constructed so as to be compatible for attachment to any known analyzer unit.

The present device is housed within a portable carrying/travel case such as a PELICAN case wherein all of the working components of the unit are concealed and positioned within the case. An external sampling probe is removably attachable to the unit so as to extend exterior of the carrying case when air samples are to be taken. In addition, a removably attachable controller unit is likewise attachable to the exterior of the case for allowing a user to control the sampling operation including the sampling protocol during use. When not in use, the external sampling probe and the controller unit are stowed inside the case for transportation to and from the field. The plurality of sampling tubes are mounted side-by-side for easy access between an inlet manifold and an outlet manifold. All tubing, valves, and the electrical control system and circuitry and connections including the battery are located within the case.

One end portion of each sampler tube is connected to a valve associated with the inlet manifold and the opposite end portion of each respective sampler tube is held in position within a hinged retainer bar mechanism which pivotally opens to allow for easy connection and removal of each respective tube. In addition, the opposite end portion of each respective tube sampler in the vicinity of the hinged retainer bar is attached to tubing which feeds through appropriate openings in a main system plate to the underside portion thereof for connection to the outlet manifold. The inlet and outlet manifolds each house a plurality of solenoid valves, one associated with the inlet portion and one associated with the outlet portion of each respective sample tube, for controlling both a purging operation and the sampling operation where air flow passes through a respective sample tube for collecting the trace element samples therewithin. A spare set of clean sample tubes are likewise housed within a storage compartment within the traveling case. The spare set of sample tubes increase the flexibility and usability of the present device in a contaminated area.

Two LED indicator lights are associated with each respective tube within the traveling case except for the type 5 cartridge tube wherein only one LED indicator light is necessary. One of the two LED indicator lights will illuminate when a 3 second (5 mL) sample has been taken with that respective tube and the other LED indicator light will indicate when a 60 second (100 mL) sample has been taken with that respective tube. If no light is illuminated for a particular tube, the unlit lights will indicate that the tube is ready for sampling.

Sampling occurs by pushing one of at least three respective buttons associated with a controller unit which is removably attachable to the outside of the case for operative use. In this regard, the controller unit will control the respective inlet and outlet valves allowing samples to be directed to the appropriate tube. To accomplish this task, the present device includes an electronic control system with appropriate programming, microprocessors and electronics to sequence the sample air flow in a predetermined manner from one tube to another tube until all of the sample tubes have been filled with a trace element. The valving associated with the intake and outlet manifolds in conjunction with the controller unit and the electronic control system will direct the air sample flow to only one sample tube at a time and for a given time interval as selected by the user. Sampling occurs by pushing one of the three respective buttons associated with the controller unit, namely, a button labeled 3-SEC, a button labeled 60-SEC, and a button labeled type 5. When the 3 second button is pushed, a 5 second purge cycle will occur for the respective tube in use and air drawn into the exterior sampling probe by the pump will flow through the inlet probe, through the inlet manifold, through a portion of the inlet valve associated with the respective tube, and through the pump and the exhaust port associated therewith. This 5 second purge cycle cleans and clears the inlet manifold and associated valves from possible prior contaminants before drawing the air sample through the respective tube for collection. Once the 5 second purge cycle has terminated, both the inlet and outlet valves associated with the next respective tube to be used are opened, and the sample air flow will be drawn by the pump into the inlet probe and through the respective sample tube for collection therein. As the air sample flows through the collection tube, it will exit the sample tube through the outlet manifold and will likewise be cycled through the pump and exit the exhaust port associated therewith.

In a like manner, if the 60-second cycle button is engaged on the controller unit, the same 5-second purge cycle will occur and thereafter the same flow path for the sampling air will take place except that air flow will be drawn through the respective sample tube for a period of 60 seconds. In similar fashion, if the type 5 button is pushed, the same 5 second purge cycle will occur and thereafter one liter of air will be pulled through the type 5 cartridge in a 60 second cycle duration. The control unit likewise includes an LED light. This light will be steady when the present device is ready for use, flashing during a sampling operation, or it will remain unlit when all tubes have been used or the battery is disconnected or discharged.

Once all of the samples have been collected, the operator can exit the sample area and return to a remote location wherein the respective sample tubes can be removed for analysis. At this time, the operator can remove each individual tube used to collect a sample, record the tube number, and record relevant sample information associated with each respective tube such as the type of sample taken, namely, a 3 second or a 60 second sample. Once all of the tubes have been removed, a reset button is pushed to reset the controller unit to tube position number 1 and to cancel the LED indicator lights thereby readying the unit for the next tube set. At this time, a new set of sampling tubes can be attached to the inlet and outlet manifolds and new additional spare tubes can be stored inside the case for future use. Each time a sample is taken by pressing one of the three buttons associated with the controller unit, the purge cycle purges any residue trace elements which may reside in the inlet manifold and its associated inlet valves prior to directing the sample flow to the next appropriate tube. In addition, the electronic control system automatically controls the sequence of tubes based upon the number of samples taken. In other words, the system through operation of the controller unit will start with tube number 1 and will cycle through tube number 7 based upon the number of samples taken. If the type 5 button is depressed, the controller will automatically open the appropriate inlet and outlet valves to the type 5 tube.

In another embodiment, it is desirable to construct and configure at least some of the sample tubes for compatible attachment to the HAPSITE field portable mass spectrometer. This means that once an individual sample tube is removed from the present device, because of the tube configuration, such tube can be immediately attached to a HAPSITE portable mass spectrometer for field analysis at a remote location. In this regard, it is recognized and anticipated that the individual sample tubes can likewise be configured and constructed for compatibility with any known analyzing unit.

In addition, the present device may likewise include a heated inlet manifold and sample flow path so as to prevent contaminant accumulation and carryover; it may include a voice recorder operable from the controller unit or other location to allow audible collection of data and information such as recording location, sample identification, time and so forth; it may include a clean cycle option with a filter such as a charcoal filter valved into the inlet flow path and heating of the sample flow path to allow post-sampling purging to remove ambient contaminants after a sampling operation at a contaminated site; and it may include mechanisms to convert the present device to a desorbing auto sampler by adding an interface to instruments such as common gas chromatographs and mass spectrometers. This would include individual heated tubes, a heated exit transfer line, and a port to accept a controlled inert gas flow source. In this particular embodiment, the sampler tubes would not need to be operator replaceable and could be more tightly spaced.

In hazardous spill first responder situations and in potential chemical agent exposure situations, the present device will allow more samples to be taken in less time thereby allowing field personnel to spend less time in a potentially hazardous environment. The present device is also lighter and more easily carried by a first responder as compared to other known units. Once samples are taken, the first responder can return to a safe location where analysis can be conducted.

These and other aspects and advantages of the present invention will become apparent to those skilled in the art after considering the following detailed description in connection with the accompanying drawings.

DETAILED DESCRIPTION

Figure 1:
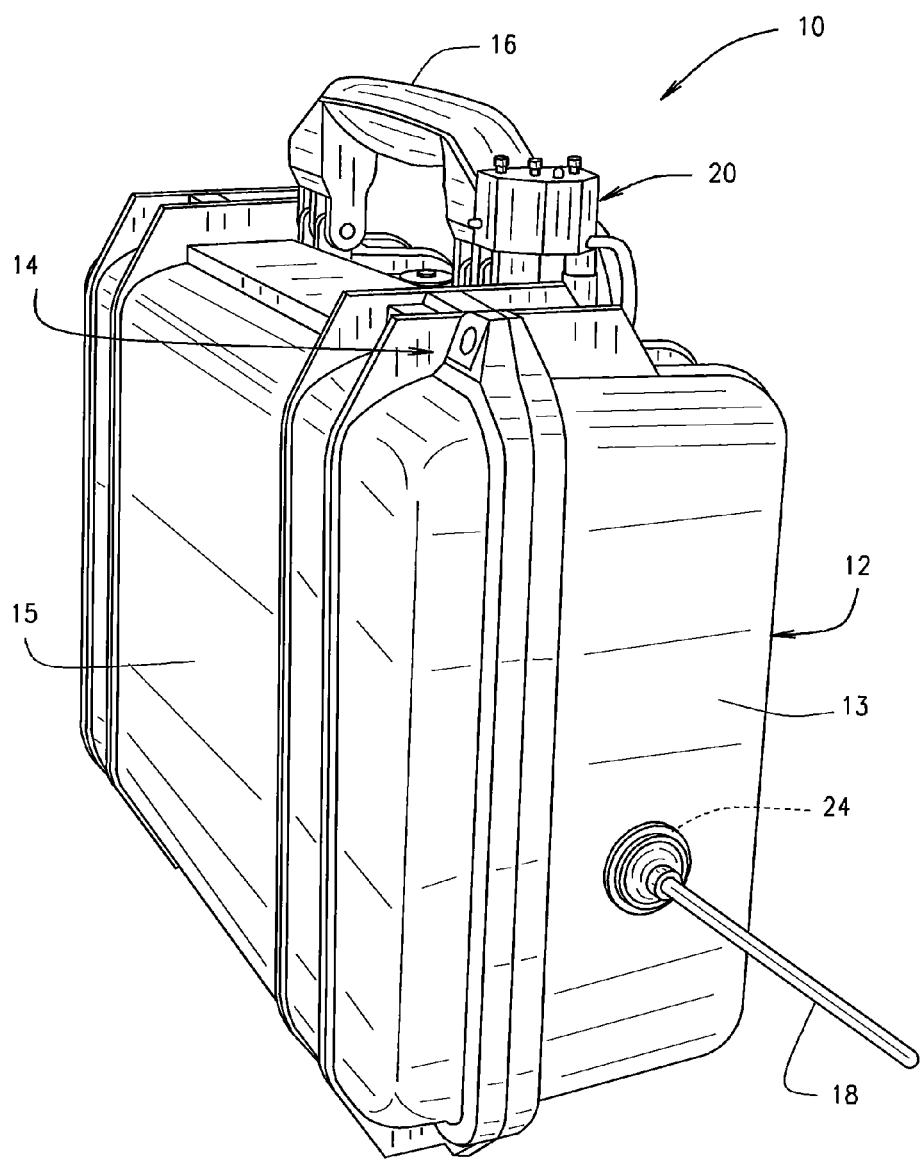
FIG. 1 is a perspective view of one embodiment of the present portable multi-tube air sampler unit constructed in accordance with the teachings of the present invention.

Referring to the drawings more particularly by reference numbers wherein like numerals refer to like parts, the number 10 in FIG. 1 identifies one embodiment of the present portable multi-tube air sampler device constructed according to the teachings of the present invention. The present multi-tube air sampler device 10 includes a lightweight portable carrying case or travel case 12 which houses all of the working components of the present device as will be hereinafter further explained. The carrying case 12 is preferably weather resistant and sufficiently rugged so as to withstand repeated field use including travel to and from a plurality of different types of contaminated environments. The case 12 opens and closes in a conventional manner similar to a typical briefcase or travel/luggage type case and includes a lower carrying case portion 13 and a top case portion 15. The carrying case portions 13 and 15 may be hingedly attached to each other in a conventional manner, or the top portion 15 may be completely removable from the lower portion 13. In either event, the case 12 opens and closes to allow access to the interior components and includes conventional open/close means 14 to accomplish this purpose. The case 12 likewise includes a handle member 16 for both carrying the case 12 to and from field operations as well as for holding the device 10 during operative use in the field when collecting multiple samples for analysis.

The present device 10 is specifically designed to be used in the field in its closed position as illustrated in FIG. 1 and, in this regard, further includes a removably attachable external sampling probe 18 for drawing ambient air into the present device 10 from the ambient atmosphere surrounding the particular environment under investigation for collection and subsequent analysis as will be hereinafter further explained. The present device 10 likewise includes a removably attachable controller unit 20 for enabling an operator to control the sampling operation and to select the appropriate sampling protocol from outside the carrying case 12. In operation, air samples are drawn from the sample environment through the external probe 18 into case 12 for collection therewithin as will be hereinafter explained and a user will manipulate the controller unit 20 to achieve the desired sampling protocol. All sampling operations can be controlled through controller unit 20 which is unpluggable and detachable from the travel case 12 for storage inside the case when the overall device 10 is not being used.

Figure 2:
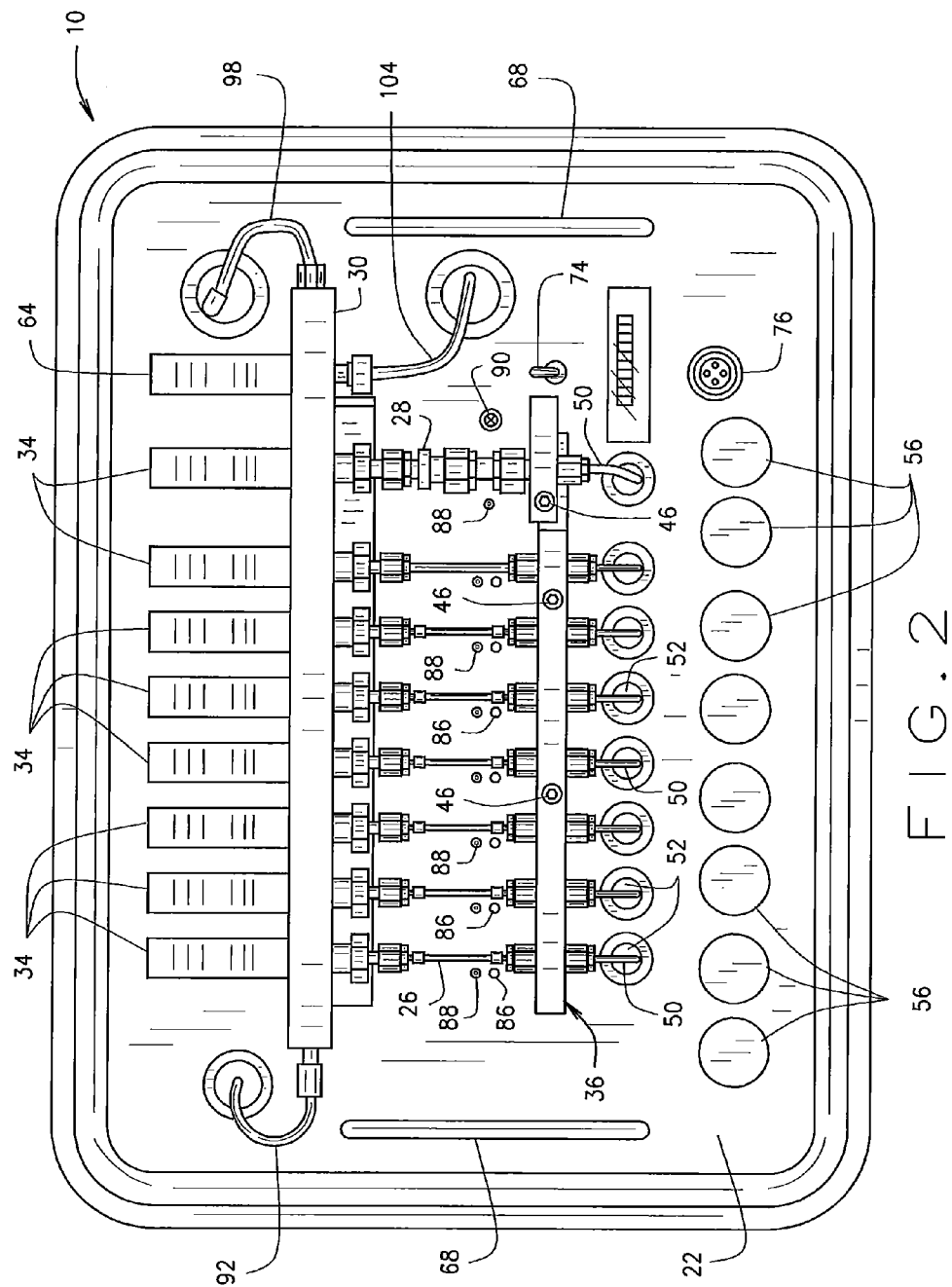
FIG. 2 is a top plan view of the present multi-tube air sampler unit looking down into the carrying case illustrated in FIG. 1 when in its open position.
Figure 3:
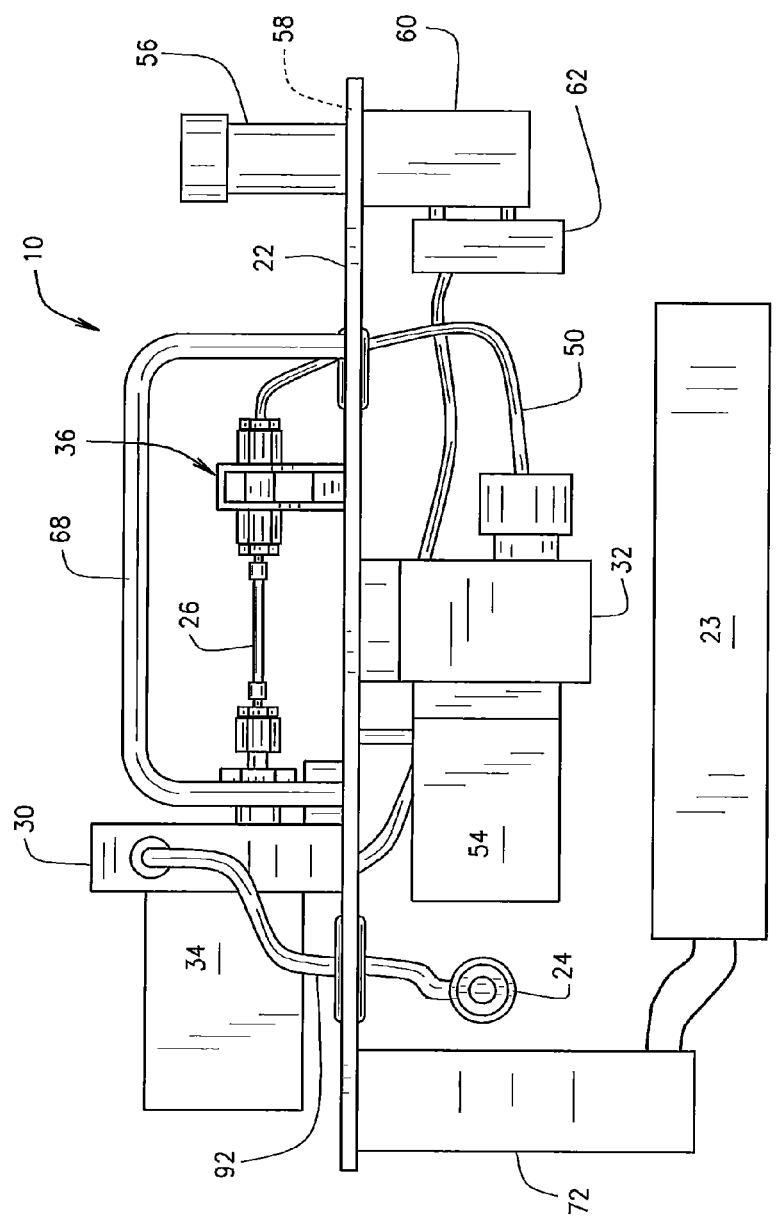
FIG. 3 is a partial side elevational view of FIG. 2 showing some of the components of the present multi-tube air sampler unit extending above and below the main system plate illustrated in FIG. 2.

In one embodiment, the carrying case 12 is a PELICAN 1450 case which is equipped with an interior panel frame (not shown) that provides a location for attaching the main system plate 22 illustrated in FIG. 2 to which most of the unit components are attached. The panel frame is positioned and located slightly below the opening lip of the case and the main system plate 22 is bolted directly thereto. All of the unit hardware, except for the battery holder and the external probe attachment point, are attached to the main system plate 22. A custom designed battery holder (not shown) bolts to the inside of the case beneath the main system plate 22 for holding the battery 23 (FIG. 3). The external sampling probe 18 is connected to the inlet manifold 30 via a luer-lock connector positioned in a recessed inlet port 24 located accessibly to the outside of the case 12 (FIG. 1). When not in use, the exterior sampling probe 18 will be removed and the controller unit 20 will be unplugged, and uncoupled from the case 12 and both components will be stowed inside the carrying case. Inlet port 24 may then be covered by installation of a removable plug (not shown) for protection from the external environment during transport. There is storage capacity in the case 12 for a spare set of sampling tubes 26 and 28 as will be hereinafter further explained, for the controller unit 20, for the external sampling probe 18, and for a set of wrenches used to install and remove the sampling tubes as will likewise be hereinafter explained. The main system plate 22 may likewise include a pair of handle members 68 for removing and replacing main system plate 22 into and out of the carrying case 12, and for providing access to the battery 23.

FIG. 2 is a top plan form view looking down into the carrying portion 13 of carrying case 12 when the top portion 15 has been opened and/or removed. Internally, a plurality of sampling tubes 26 and 28 are connected to an inlet manifold 30 and an outlet manifold 32 as will be hereinafter further explained, the outlet manifold 32 being located below the main system plate 22 and being positioned parallel to the inlet manifold 30 as best illustrated in FIG. 3. In the particular embodiment illustrated in FIGS. 2-4, the plurality of tubes 26 include seven Tri-bed tubes which are mounted side-by-side for easy access and tube 28 is a Type 5 cartridge tube which is likewise mounted along side tubes 26 for easy access. One end portion of each of the respective tubes 26 and 28 is physically connected and/or attached directly to a corresponding valve associated both with each respective tube 26 and 28 and with the intake manifold 30 as best illustrated in FIGS. 2 and 3. This attachment can be by any suitable conventional means such as a threaded engagement as illustrated.

Figure 4:
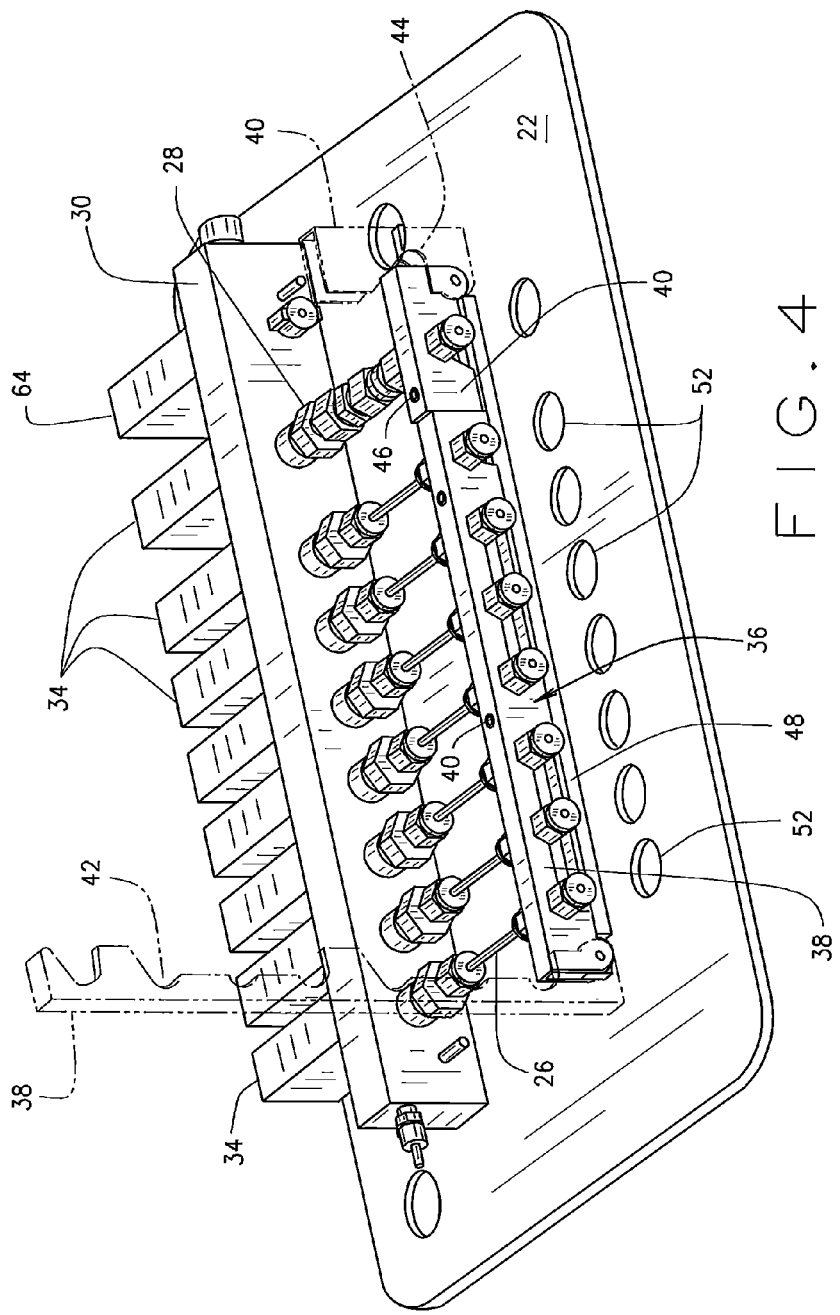
FIG. 4 is a partial perspective view of some of the components illustrated in FIG. 2 showing the hinged retainer bar in both its open and closed positions.

On the other hand, the opposite end portion of each respective tube 26 and 28 is held in operative position within a hinged retainer bar assembly 36 as best illustrated in FIGS. 2 and 4. In this regard, the hinge retainer bar assembly 36 includes two pivotable members 38 and 40, pivotable member 38 being pivotally attached at one end portion of the assembly 36 and including a plurality of slots, concaved portions or cutouts 42 for engaging and holding the opposite end portion of each respective tube member 26 in its respective operative fixed position as illustrated in FIGS. 2-3. The pivotable bar member 38 extends across all of the tubes 26 and the slots or cutout portions 42 are appropriately spaced so as to engage the respective opposite end portion of each of the tubes 26 when the tubes 26 are attached to the intake manifold 30 and their corresponding valves 34. In similar fashion, retainer bar member 40 is pivotably attached at the opposite end portion of the assembly 36 from bar member 38 and, in the embodiment illustrated in FIG. 4, is designed to hold and retain only the type 5 cartridge tube 28. Like retainer bar member 38, bar member 40 likewise includes a slot, concave portion or cutout 44 for mating with and engaging the opposite end portion of the type 5 cartridge tube 28.

The hinged retainer bar assembly 36 is designed to allow for quick and easy removal and replacement of the various sample tubes 26 and 28. For example, if any one or more of the tubes 26 need to be removed from the present device 10 for either replacement and/or analization of the trace elements captured therewithin, hinged retainer bar member 38 is unlocked and pivoted upwardly as shown in dotted outline form in FIG. 4 and any one or all of the opposite end portions of the respective tubes 26 are now free from attachment and are no longer held in a fixed position within the carrying case 12. Once hinged retainer bar member 38 is moved to its open position, the opposite end portion of the respective tubes 26 can be unfastened, unthreaded, or de-attached from the intake manifold 30 using a wrench set stored in the case 12 for total removal of the respective tube 26 from the present device 10.

In similar fashion, if only the type 5 cartridge tube 28 needs to be removed from the present device, only the hinged retainer bar member 40 need be pivotally rotated to its open position as shown in dotted outline form in FIG. 4 thereby uncoupling the opposite end portion of the type 5 cartridge tube 28 from the present device. Similarly, the opposite end portion of the type 5 cartridge tube 28 can then be easily unfastened, unthreaded and/or de-attached from the inlet manifold 30 for complete removal of the tube 28 from the present device 10. When in their respective closed positions, the hinged retainer bar members 38 and 40 can be locked into their closed positions using any suitable attachment/locking mechanism such as the threaded fasteners 46 illustrated in FIG. 2. The respective tubes 26 and 28 may likewise mate with and lie on top of a support member 48 as best illustrated in FIG. 4. The parallel positioning of the inlet and outlet manifolds 30 and 32 and the positioning of the hinged retainer bar assembly 36 as best illustrated in FIG. 3 allows optimally short unpurged sample paths between tubes 26 and 28 and corresponding inlet valves 34 mounted on inlet manifold 30 to be achieved while also allowing tubes 26 and 28 to be operatively fixed within the case 12 and use of the hinged retainer bar assembly provides for quick and easy attachment and removal of the sample tubes since only one end of each tube needs to be directly fastened to the inlet manifold 30. It is also recognized and anticipated that the assembly 36 may include a single pivotal member extending across all of the tubes 26 and 28, or any plurality of such pivotal members depending upon the total number of sample tubes being housed within the case 12.

Referring again to FIGS. 2-4 and 6A-6C, the inlet manifold 30 has associated therewith a plurality of solenoid valves 34, one valve 34 being associated with each respective sample tube 26 and 28. Once one end portion of the respective tubes 26 and 28 are attached to the inlet manifold 30 and to their respective valves 34 as previously explained, sample air can be directed to any one of the tubes 26 and 28 as will be hereinafter further explained. The opposite end portion of each respective sample tube 26 and 28 in the vicinity of the hinged retainer bar 36 is likewise attached to tubing 50 which feeds through appropriate corresponding openings 52 to the underside portion of the main system plate 22 for connection to the outlet manifold 32 as best illustrated in FIGS. 2 and 3. The tubing 50 can be associated with a quick disconnect or other attachment mechanism such as with a threaded compression fitting for quickly attaching and unattaching the tubing 50 to a respective sample tube 26 and 28. The inlet manifold 30 houses the respective solenoid valves 34 each of which are connected to the inlet portion of each respective sample tube 26 and 28. In this regard, one example of a suitable solenoid valve for use in the present device 10 is the Burkert type 6606 solenoid valve which includes low dead volume, an isolating diaphragm, and internal wetted surfaces consisting of PEEK and FFKM polymers. These valves are typically 3-way valves although other valves can likewise be used.

Figure 6A:
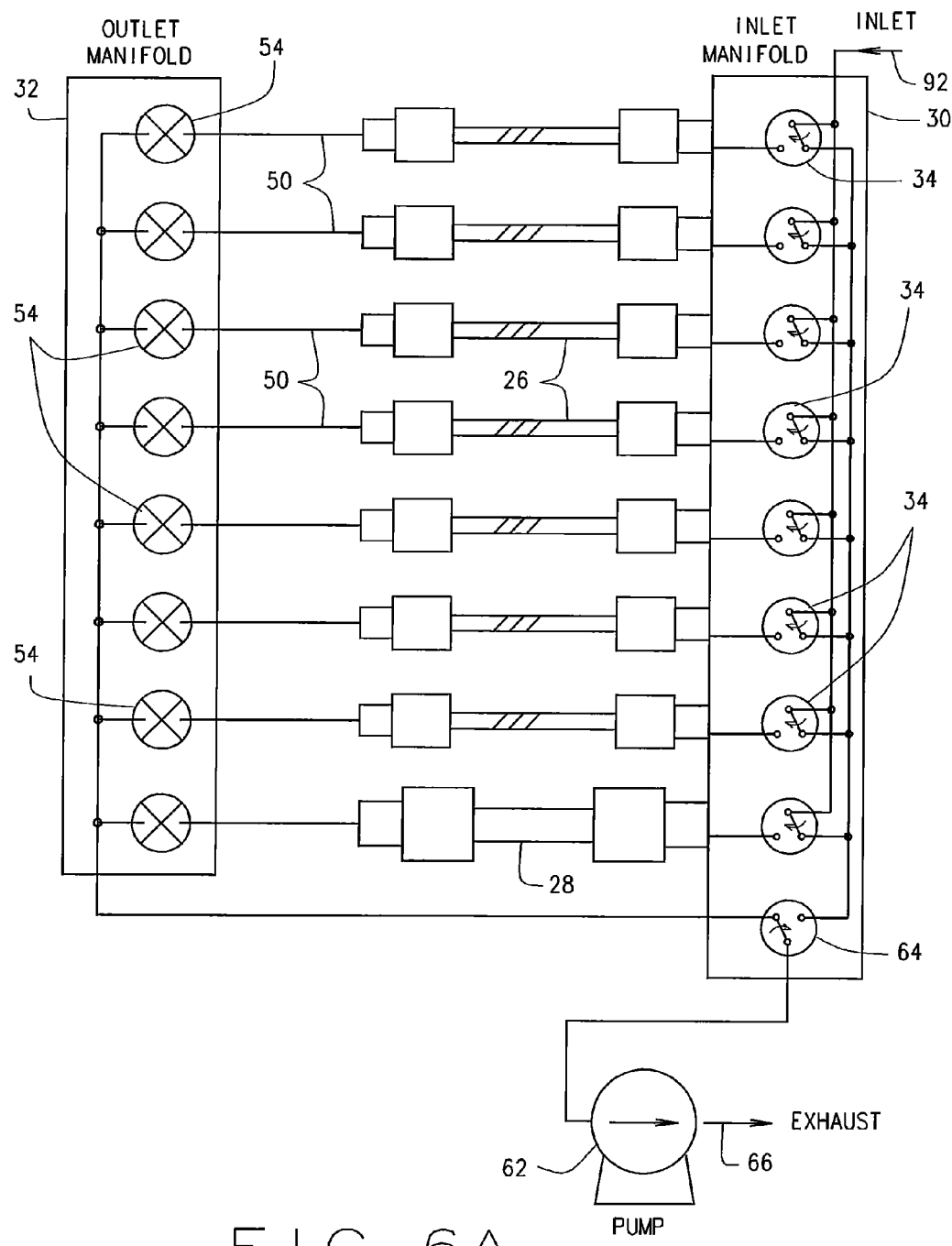
FIG. 6A is a schematic representation of the valving arrangement associated with the inlet and outlet manifolds of the present multi-tube air sampler unit in their closed condition.
Figure 6B:
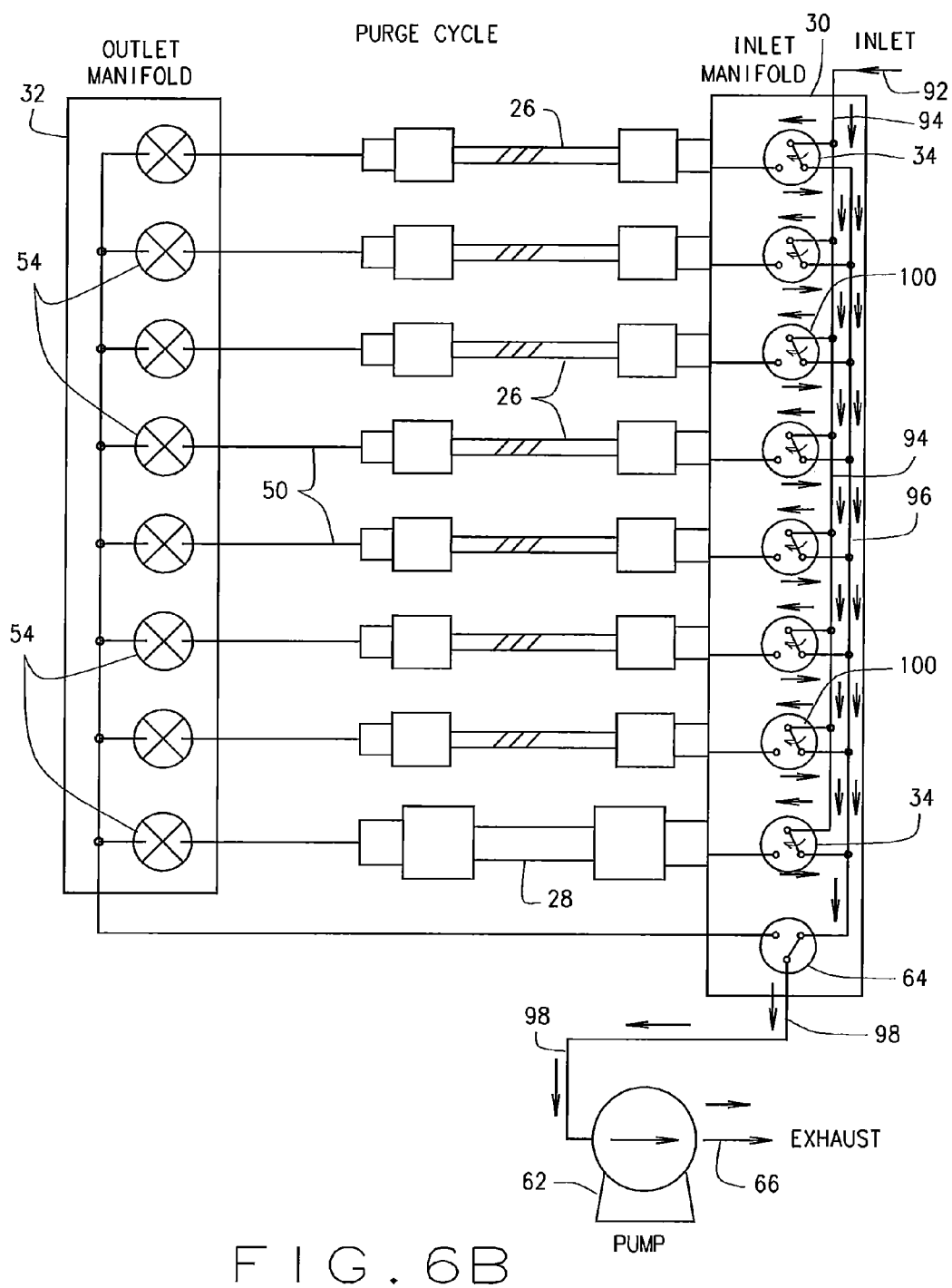
FIG. 6B is a schematic representation similar to FIG. 6A showing the valving arrangement for the purge cycle.
Figure 6C:
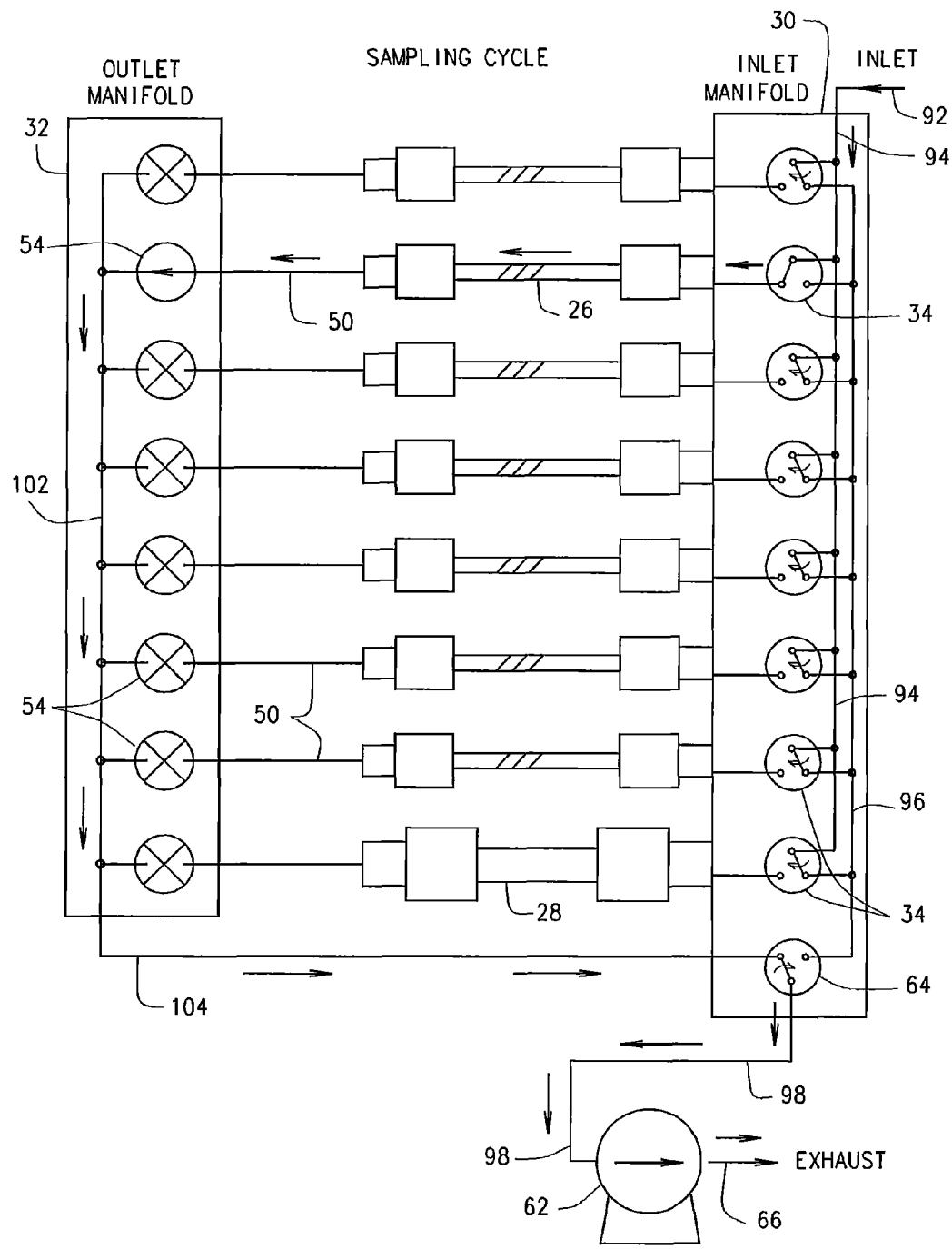
FIG. 6C is a schematic representation similar to FIG. 6A showing the valving arrangement for a typical sampling cycle.

Still further, as best illustrated in FIGS. 6A, 6B and 6C, the present device 10 likewise includes a plurality of 2-way solenoid valves 54 associated with the outlet manifold 32, a respective solenoid valve 54 being likewise associated with the outlet portion of each respective tube 26 and 28. The valves 54 control the exit or outflow of an air sample passing through a respective tube for collecting trace elements therewithin. The complete operation of the schematic diagrams illustrated in FIGS. 6A, 6B and 6C will be hereinafter later discussed.

As best illustrated in FIG. 2, the present device 10 further includes a spare set of clean sample tubes 26 and 28 that can be stored inside the carrying case 12 in protective containers or canisters 56 located adjacent one side portion of the carrying case 12. Each container 56 is slidably receivable within a corresponding opening 58 extending through the main system plate 22 as best illustrated in FIG. 3. The respective containers 56 rest within the holder member 60 associated with the underside portion of the main system plate 22 as likewise illustrated in FIG. 3. The respective sample tubes 26 and 28 are stored within the protective containers 56 and can be used in the field to take additional samples over and above the plurality of tubes 26 and 28 connected to the inlet and outlet manifolds 30 and 32 respectively, or such spare tubes can be used to replace the tubes 26 and 28 when such tubes are disengaged from the present device 10 for analysis purpose. In such an event, clean additional spare tubes 26 and 28 can be easily replaced and stored in the containers 56.

Referring again to FIGS. 2-4, a pump 62 (FIG. 3) is utilized to draw air samples from the ambient atmosphere into the external sampling probe 18 and through one of the respective sample tubes 26 and 28 at a time as will be more fully explained with respect to FIGS. 6A, 6B and 6C. A 3-way solenoid pump valve 64 (FIG. 2) controls the air flow path through the inlet and outlet manifolds 30 and 32 depending upon the protocol selected, the position or state of valve 64 controlling the flow path for either a purging operation or a sampling operation as will be explained hereinafter with respect to FIGS. 6A, 6B and 6C. The pump 62 likewise includes an exhaust port illustrated by arrow 66 in FIGS. 6A-6C for allowing the sample air flow to exit the device 10.

Figure 5:
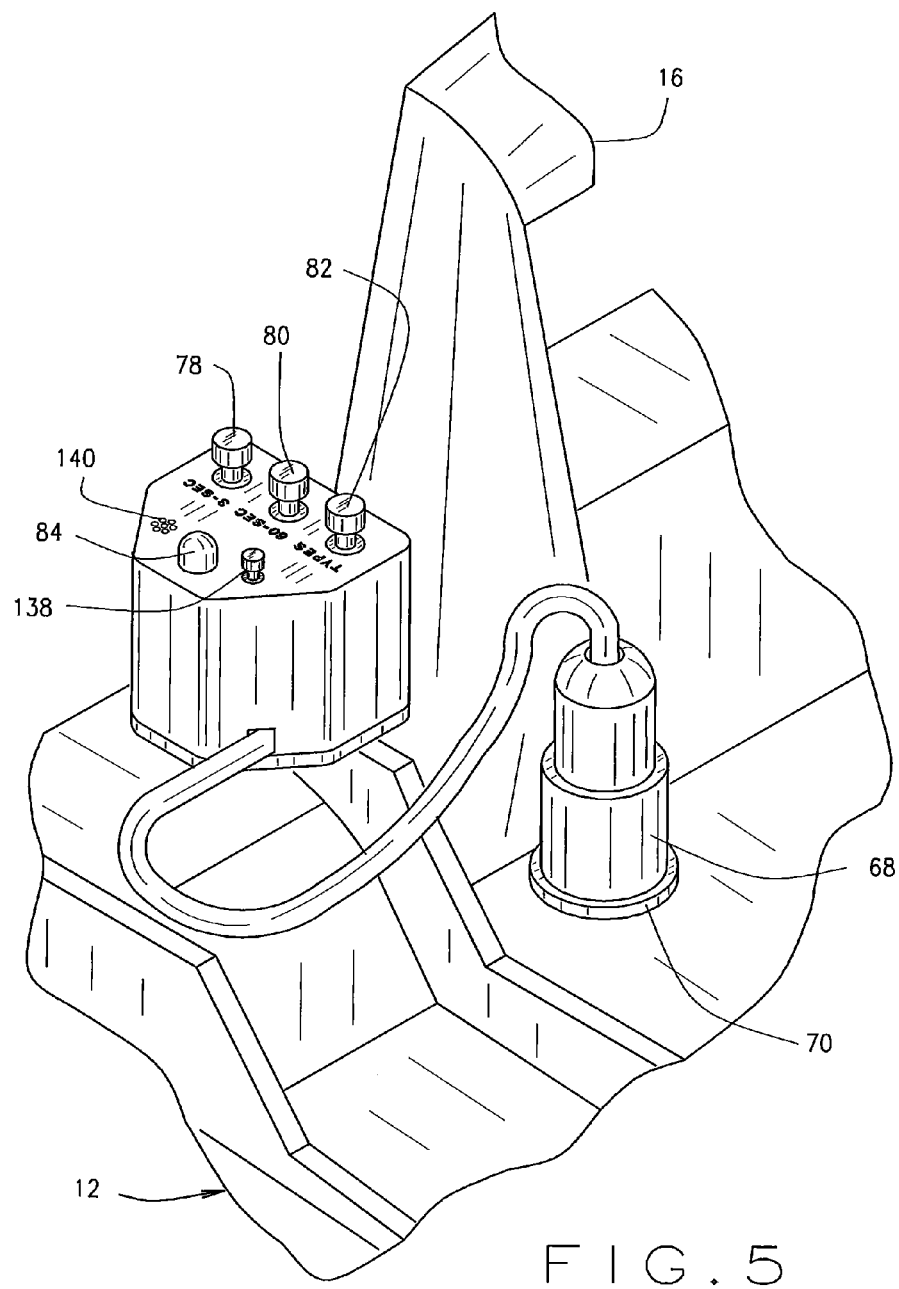
FIG. 5 is a partial perspective view of the top portion of the carrying case illustrated in FIG. 1 illustrating the removably attachable controller unit.

The sequencing of the respective solenoid valves 34 and 54, the sequential selection of the appropriate sample tubes 26 and/or 28 to which flow is initiated, the flow rate induced by the pump 62, and the duration of the sample flow through a given sample tube 26 or 28, is controlled by the control unit 20 which is electrically connected to appropriate microprocessors, software and other electronic/computer related equipment such as electronic control system 72 (FIG. 3) to carry out the functionality of the present device as will be hereinafter explained. The controller unit 20 is portable and is removably attachable to the exterior portion of the carrying case 12 near the handle portion as best illustrated in FIGS. 1 and 5 such that the entire device 10 can be operable from outside the case 12. The controller unit 20 includes a removably attachable plug connection 68 which is electrically connective to a corresponding female input socket or port 70 associated with case 12, the input socket 70 being electrically connective to the electronic control system 72 (FIG. 3) associated with the present device 10. Once the power switch 74 (FIG. 2) is activated, power to the entire device 10 turns on automatically when the controller unit 20 is plugged into the input socket 70. A single 14 volt Lithium Ion battery 23 from OceanServer, with matching power conversion and charging hardware, is housed below the main system plate 22 inside the carrying case 12 and powers the entire device 10. The battery 23 may be charged by connecting an external power supply to a port 76 (FIG. 2) located on the main system plate 22.

The controller unit 20 is best illustrated in FIG. 5 and controls the operation of the sampling protocol and, in the embodiment illustrated, includes at least 3 buttons for controlling the sampling protocol and 1 LED light. Sampling trace elements from a particular environment or ambient atmosphere occurs by pushing one of the 3 respective buttons 78, 80 or 82 associated with the controller unit 20. Button 78 is labeled 3-SEC and, when pushed, activates a 5 second purge cycle followed by a 3 second sampling cycle at 100 milliliters per minute on the next available tube 26. The 5 second purge cycle will allow air drawn into the exterior sampling probe 18 to flow through the inlet probe, through the inlet manifold 30, through the inlet portion of each of the respective inlet valves 34, through the pump valve 64, through the pump 62 and out the pump exit port 66 for exhaustion outside of the case 12. A detailed explanation of the purge cycle as well as the sample flow cycle through a particular tube 26 and 28 will be discussed in more detail with respect to FIGS. 6A, 6B and 6C. The 5 second purge cycle cleans the inlet manifold as well as the inlet portion associated with each of the respective inlet valves before drawing a sample air flow through a particular tube 26 and 28. Button 80 is labeled 60-SEC and, when pushed, likewise activates a 5 second purge cycle as previously explained followed by a 1 minute sampling cycle through the next available tube 26. In a similar fashion, button 82 is labeled type 5 and, when pushed, likewise activates a 5 second purge cycle as previously explained followed by a 1 minute sampling cycle at 1 liter per minute through the type 5 cartridge tube 28.

The controller unit 20 likewise includes an LED light 84 which, when illuminated in a steady condition, indicates that the sampler device 10 is ready to sample trace elements from a particular environment. When the LED light 84 is flashing, this indicates that sampling of a particular environment is in progress. When the LED light 84 is unlit, this indicates that all tubes 26 and 28 have been used or that there is no power to the controller unit 20.

As a result, a user of the present device 10 can completely control the sampling protocol from the exterior of the carrying case 12 by merely controlling and manipulating the buttons 78, 80 and 82 associated with controller 20. As such, once the 5 second purge cycle has terminated with respect to each different sampling protocol, namely, a 3 second sampling cycle for tube 26, a 60 second sampling cycle for tube 26, or a 60 second sampling cycle at 1 liter per minute for the type 5 cartridge tube 28, both the inlet and outlet valves 34 and 54 respectively associated with the next respective tube 26 or 28 to be used are opened and air flow will be drawn by the action of the pump 62 into the inlet probe 18 and through the respective sample tube 26 or 28 for the selected sampling cycle period of time. As the air flow passes through the appropriate sample tube 26 or 28, the sample air flow is then again exhausted through the pump 62 and out the exhaust port 66 associated therewith as will again be hereinafter further explained. Regardless of which controller button is activated, the same 5 second purge cycle will occur and the same sample flow path will take place through a selected sample tube except that the air flow will be drawn through the respective tube for either a 3 second cycle, a 60 second cycle, or if the type 5 cartridge is selected, one liter of air will be pulled through the type 5 cartridge in a 60 second cycle. When the device 10 is not in operative use, the controller 20 can be unplugged from the input socket 70 and stored within the carrying case 12.

The present device 10 further includes a pair of LED lights associated with each of the tubes 26, and a single LED light associated with the tube 28. One of the respective LED lights such as the light 86 will illuminate when a 3-second sampling cycle has been used with a respective tube. In other words, illumination of light 86 indicates that a sample air flow of trace elements from the particular environment has been passed through that particular sample tube 26 for a 3 second period of time. The other LED light 88 associated with each of the respective tubes 26 and with the tube 28 illuminates when a 60 second or one minute sampling cycle has been passed through a respective tube 26 or 28. The LED lights 86 and 88 are mounted next to the respective sampling tubes as best illustrated in FIG. 2 and when a particular tube has been used, a corresponding LED light 86 or 88 illuminates and remains illuminated until the device 10 is reset. The states of the respective LED lights are latched for preservation during power down so that upon reapplication of power they will again display the current state of each respective tube 26 and 28. These lights are advantageous to a user because they indicate the duration of the sampling cycle associated with each sample specimen when the device 10 is removed to a remote location for analysis. Once all of the samples have been collected and a user opens the carrying case 12 to remove the respective sample tubes for analysis, the illuminated LED lights 86 and 88 will allow the operator to record the type of sample taken with each tube removed for analysis. An unlit LED light 86 and 88 will indicate that no sample has been taken with that respective tube and that that tube is ready for sampling. A reset button 90 is also positioned on the main system plate 22 as best illustrated in FIG. 2 which, when activated, allows a user to cancel the LED indicator lights 86 and 88 thereby readying the device 10 and the LED lights 86 and 88 for use with the next set of sample tubes to be inserted within the device 10. The reset button 90 likewise resets the controller unit 20 and the associated electronics 72 for supplying the incoming sample air flow to tube position number 1 for sequentially collecting air samples within the respective tubes 26 and 28. The reset button 90 therefore allows a user to reset the entire device 10 after installing a fresh set of sampling tubes for further testing. The LED lights 86 and 88 can be color-coded to further assist the operator in identifying the sampling cycle associated with each respective tube.

FIG. 6A is a schematic representation of the operative configuration of the sample tubes 26 and 28, the inlet and outlet manifolds 30 and 32, the inlet and outlet valves 34 and 54, the pump valve 64 and the pump 62. As illustrated, an inlet valve 34 is associated with the inlet side of each respective tube 26 and 28 and an outlet valve 54 is associated with the outlet side of each respective tube. The inlet valves 34 are associated with the inlet manifold 30 and the outlet valves 54 are associated with the outlet manifold 32. The valves 34, 54 and 64 control the direction of the sample air flow through the inlet and outlet manifolds during both the purging cycle and the sampling cycle. A pump valve 64 is likewise associated with the inlet manifold 34. In the configuration illustrated in FIG. 6A, all of the valves are positioned in their closed position. Inlet flow path 92 is connected to the external sample probe 18 for allowing the sample intake flow to enter the inlet manifold 30. As best illustrated in FIG. 3, the external sample probe 18 is connected to the recessed port 24 and travels through inlet tubing 92 to the inlet manifold 30. If the pump 62 were activated with all of the respective valves 34, 54, and 64 in their closed position as illustrated in FIG. 6A, no suction or drawing force will be applied to the external sample probe 18 since the pump valve 64 is in its closed position, and likewise no suction or drawing force will be applied to the sampling tubes 26 and 28 since the outlet valves 54 are in their closed position. Further, sampling tubes 26 and 28 are not exposed to ambient air since inlet valves 34 are in their closed position.

FIG. 6B is a schematic representation of the valving arrangement associated with the inlet and outlet manifolds 30 and 32 during a purging cycle. When any one of the controller unit buttons 78, 80 or 82 are initially pushed, a 5 second purge cycle is activated so as to purge any residual trace elements which may reside in the inlet manifold 30 and in the inlet portion of each respective valve 34 from the last sampling operation. This purge cycle occurs when any one of the controller buttons 78, 70 or 82 are pushed. The purge cycle is activated via the electronic control system 72 by opening pump valve 64 as illustrated in FIG. 6B thereby allowing the pump 62 to draw a sample air flow into and through the external sample probe 18 via flow paths 92, 94, 96 and 98 associated with the inlet manifold valving arrangement. This allows a sample intake flow to travel via inlet flow path 92 and via flow path 94 through the inlet portion 100 associated with each respective inlet valve 34. Some of the sample intake air flow will pass through the inlet valve portion 100 and exit via flow path 96 whereas some of the sample intake air flow will pass directly via flow path 96 through the pump valve 64 to pump 62. This valving arrangement allows the 5 second purge cycle to purge any residual trace elements which may reside in flow paths 92, 94, 96, 98 and 100 prior to directing the sample air flow to the next appropriate tube. This same purge cycle will occur each time one of the controller buttons 78, 80 or 82 is activated. Once the purge cycle is completed, the controller unit 20, through its associated electronic control system 72, will automatically close pump valve 64 and control the sequence of the tubes based upon the number of samples taken and will automatically control the opening and closing of the appropriate valves 34 and 54 so as to direct the sample intake air flow to the next available tube 26 or to the tube 28.

FIG. 6C is a schematic representation of the valving arrangement associated with the inlet and outlet manifolds 30 and 32 during a particular sampling cycle once the 5 second purge cycle has been completed. As illustrated in FIG. 6C, once the purge cycle is completed, pump valve 64 moves to its closed state and the next available sample tube 26 or 28 will be selected and the appropriate inlet and outlet valves 34 and 54 for that respective tube will be opened. In the representation illustrated in FIG. 6C, the second tube 26 has been selected to illustrate a typical sampling cycle. As a result, the inlet valve 34 associated with the selected tube 26 has been moved to its open state and the associated outlet valve 54 associated with the selected tube 26 has likewise been moved to its open state. This then allows the sample intake air flow to flow through the external sampling probe 18, through inlet manifold 30 via flow paths 92 and 94 to the open inlet valve 34 as illustrated. The sample air flow will then flow through the open inlet valve 34 and through the selected tube 26 and will exit through the open outlet valve 54 to flow path 102 associated with the outlet manifold 32. As the sample intake air flow passes through tube 26 and flows through outlet valve 54, such air flow follows flow paths 102 and 104 back to the pump valve 64 wherein it is diverted along flow path 98 through pump 62 to the pump exhaust port 66 associated therewith for exit from the device 10. This sampling cycle will occur for either a 3 second sampling cycle or a 60 second sampling cycle depending upon which of the controller buttons 78 or 80 are selected. If button 82 is selected, the sample intake air flow will pass through tube 28 in a similar fashion as discussed above with respect to tube 26. Once the sampling cycle is completed, the associated inlet and outlet valves 34 and 54 will close and the valving arrangement will return to the state illustrated in FIG. 6A for the next purging/sampling cycle.

The controller unit 20 controls all operations of the present device 10 and controls the sampling protocol depending upon which of the controller buttons 78, 80 or 82 is selected. The controller unit 20 through the electronic control system 72 automatically controls the operation of the valves 34, 54 and 64 and of the pump 62 and automatically controls the sequence of the tubes to collect the various samples of trace elements based upon the number of samples taken and based upon the programming, software and other electronics associated with the electronic control systems 72. In one embodiment, the electronic control system 72 is based upon a programmable interface controller microchip 16F877A. The control system includes a plurality of printed circuit board assemblies (PCB) including a control PCB, a valve LED PCB, and DC-DC converter PCB. The control PCB includes the programmable interface controller, valve and pump interface circuitry and pump speed control circuitry. Pump speed is based upon fixed set points determined to provide the correct flow rate depending upon the tube type and the sample cycle duration. In addition, the capability likewise exists to increase or decrease pump speed in the field by adjusting potentiometers located on the valve LED PCB. The valve LED PCB also includes LED indicators 86 and 88 and the system reset button 90. Battery monitoring and charging functions are likewise provided for by the control electronics. Other electronic control systems are likewise recognized and anticipated and can be used to control the operation of the present device 10. Importantly, the electronic control system 72 automatically controls the purging cycle and the selection of the appropriate sample tubes dependent upon the sampling protocol selected by the operator via controller unit 20.

Once all of the samples have been collected at a particular environment, the operator can remove the controller unit 20 and the external sample probe 18 from the exterior portion of the carrying case 12 and store such items inside the case. The operator can likewise turn off the power switch 74 and transport the entire unit with the sample tubes 26 and 28 to a remote location for analization. At the appropriate location, the operator can remove the tubes which were used for sampling, record the tube numbers and all relevant sample information including the type of sample taken such as a 3 second or a 60 second sample. The sample duration time can be obtained by activating the power switch 74 and reading the LED indicator lights 86 and 88 associated with each respective tube as previously explained. Each sample tube used can then be removed from the device 10 and analyzed using appropriate analyzing means such as the HAPSITE portable mass spectrometer or other appropriate analyzing units. Once the appropriate tubes 26 and 28 have been removed from the present device 10 for analization, the operator can push the reset button 90 thereby canceling the LED indicator lights 86 and 88 and repositioning the electronic control system 72 to tube position number 1 thereby readying the device 10 for the next tube set. At this time, the spare additional tubes carried in the tube canisters 56 can be removed and placed in operative position between the inlet and outlet manifolds as previously explained and a new additional spare set of tubes can be stored in the tube canisters 56. Once this is accomplished, the present device 10 is again ready for use in the field. When again activated for use in the field, the controller unit 20 will again start with tube number 1 and will cycle through all of the tubes 26 based upon the number of samples taken. If the type 5 button is depressed, the controller unit 20 will automatically open the appropriate inlet and outlet valves to utilize tube 28.

In another aspect of the present invention, the tubes 26 are specifically constructed and configured for compatible attachment to a HAPSITE field portable mass spectrometer. This means that once the individual sample tubes 26 are removed from the present device 10, such tubes can be immediately attached to a HAPSITE portable mass spectrometer for field analysis at a remote location. This allows the present samples to be analyzed on a known device and allows the present device 10 to be returned to the field for additional sampling while previous samples are being analyzed. In this regard, it is also recognized and anticipated that the sample tubes 26 and 28 can be specifically constructed and configured for compatible attachment to a wide variety of different known analyzing units including a wide variety of different types of mass spectrometers and gas chromatographs as well as other analyzing devices.

Figure 7:
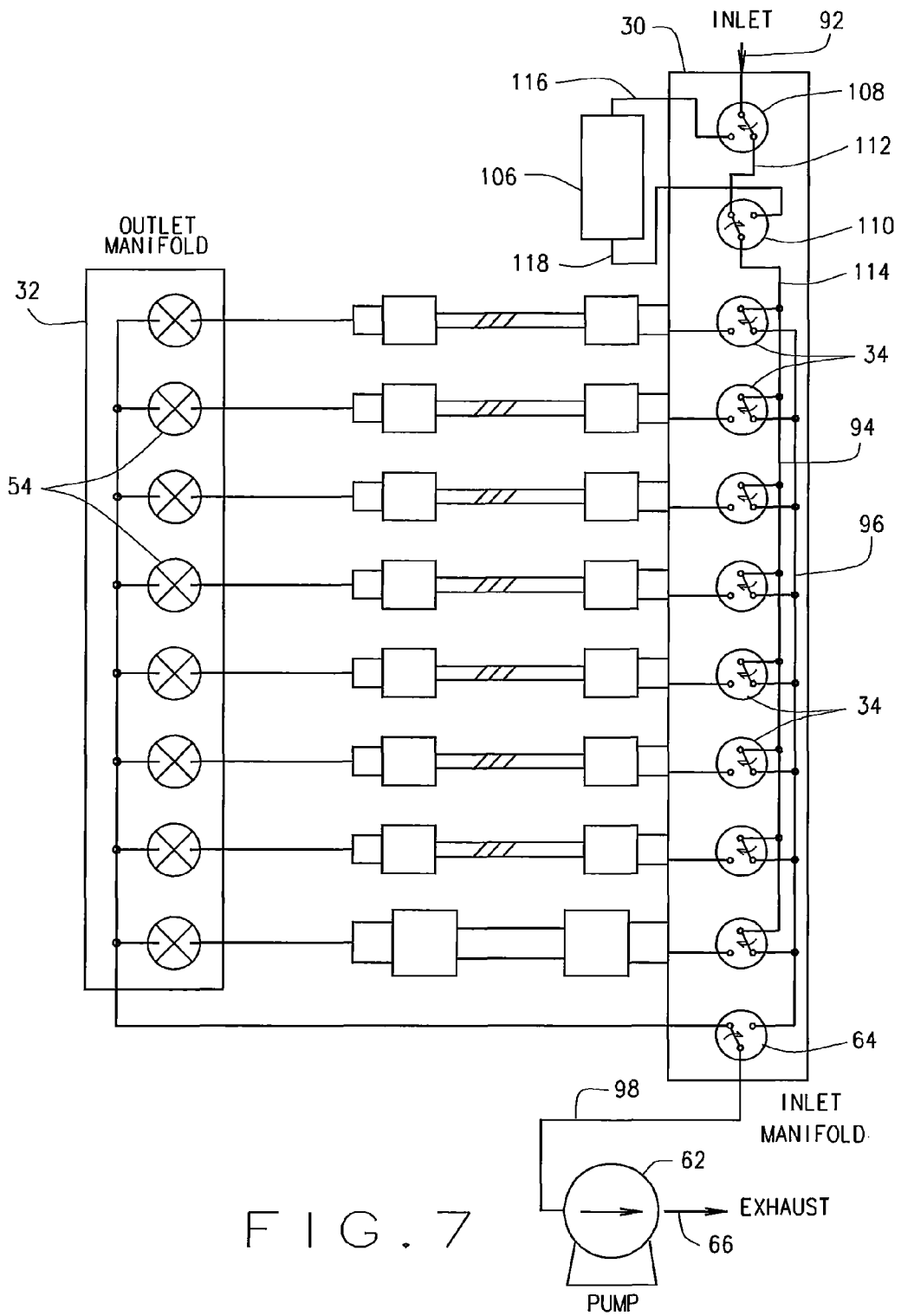
FIG. 7 is a schematic representation of another embodiment of the present multi-tube air sampler unit illustrating a clean cycle option wherein a filter device is valved into the inlet flow path to allow post-sampling purging of incoming air to remove ambient contaminants after a sampling operation has occurred at a contaminated site.

FIG. 7 is a schematic representation of another embodiment of the present device 10 illustrating a clean cycle option wherein a filter device such as a charcoal filter 106 is valved into the inlet flow path 92 of an air sample entering the inlet manifold 30 to provide an even more efficient and cleaner post-sampling purging cycle of incoming air to further remove ambient contaminants from the incoming air flow used to purge the inlet manifold 30 and its associated inlet valves 34 as previously explained. In this particular embodiment, an additional pair of solenoid valves 108 and 110 are associated with the inlet manifold 30 and are respectively connected to the inlet and outlet ports of the filter device 106, valve 108 being connected to the inlet port of filter 106 and valve 110 being connected to the outlet port of the filter 106.

In this particular embodiment, valves 108 and 110 are cycled in sequence with the pump valve 64 through the electronic control system 72 for controlling the purging cycle. In the representation set forth in FIG. 7, the pump valve 64 and the additional filter valves 108 and 110 are all shown in their closed position whereby any sample intake air flow will flow through passageway 92, through valve 108, through passageway 112, through valve 110, and through passageway 114 to flow paths 94 and 96 as previously explained with respect to FIGS. 6A, 6B and 6C. From flow path 114, the sample intake flow will migrate to the appropriate tube 26 or 28 for collection of the trace elements as previously explained with respect to FIG. 6C.

However, in contrast to the purge cycle described with respect to FIG. 6B, in the embodiment illustrated in FIG. 7, when this enhanced purge cycle is activated through activation of any one of the controller buttons 78, 80 or 82, valves 64, 108 and 110 are programmed to open thereby allowing flow paths 116 and 118 associated with the inlet and outlet ports of the filter 106 to be fluidly connected with the valves 108 and 110. In this situation, the sample air intake flow will pass through filter 106 via flow paths 92, 116 and 118 and will exit valve 110 via flow path 114 and will further migrate through flow paths 94 and 96 and through the inlet portions of each of the respective inlet valves 34 so as to exit the pump exhaust port 66 as previously explained with respect to FIG. 6B. Once the purge cycle is completed, valves 64, 108 and 110 return to their closed positions and the action of the pump 62 again draws the sample intake air in and through the inlet manifold 30 and to the appropriate tube 26 or 28 as previously explained with respect to FIG. 6C. Use of the filter 106 during the purge cycle enhances the purge cycle and adds an extra measure of protection and filtration in purging any residual trace elements which may reside in the inlet manifold and its associated valves prior to directing the sample intake air flow to the next appropriate tube. This is accomplished by filtering the incoming air flow of any contaminants through filter 106 before the purging air flow cycles through the inlet manifold 30. Operation of the valves 108 and 110 in conjunction with pump valve 64 can be easily programmed into the electronic control system 72 by a person skilled in the art.

Use of the enhanced capabilities illustrated in FIG. 7 can likewise be used during a sampling cycle to establish a base line reading of the device 10 prior to taking samples of trace elements so as to establish a base line contamination level associated with the device 10. Use of the appropriate filter 106 during a sampling cycle will tell a user whether the device is contaminated and its level of contamination by allowing a clean sample air flow to flow through one of the sample tubes 26 or 28 and thereafter analyzing such tube to determine the level of trace elements collected within the selected tube. Once this base line reading is obtained, normal sampling of the ambient atmosphere is accomplished as explained with respect to FIG. 6C, and without diverting the incoming air flow through the filter 106. Activation of the filter 106 and its associated valves 108 and 110 can be automatically programmed into the purging cycle through the electronic control system 72, or an additional switch or button can be incorporated into the controller unit 20, or elsewhere on the exterior portion of the case 12, for selective activation of filter 106 during either a purge cycle or a sampling cycle.

Figure 8A:
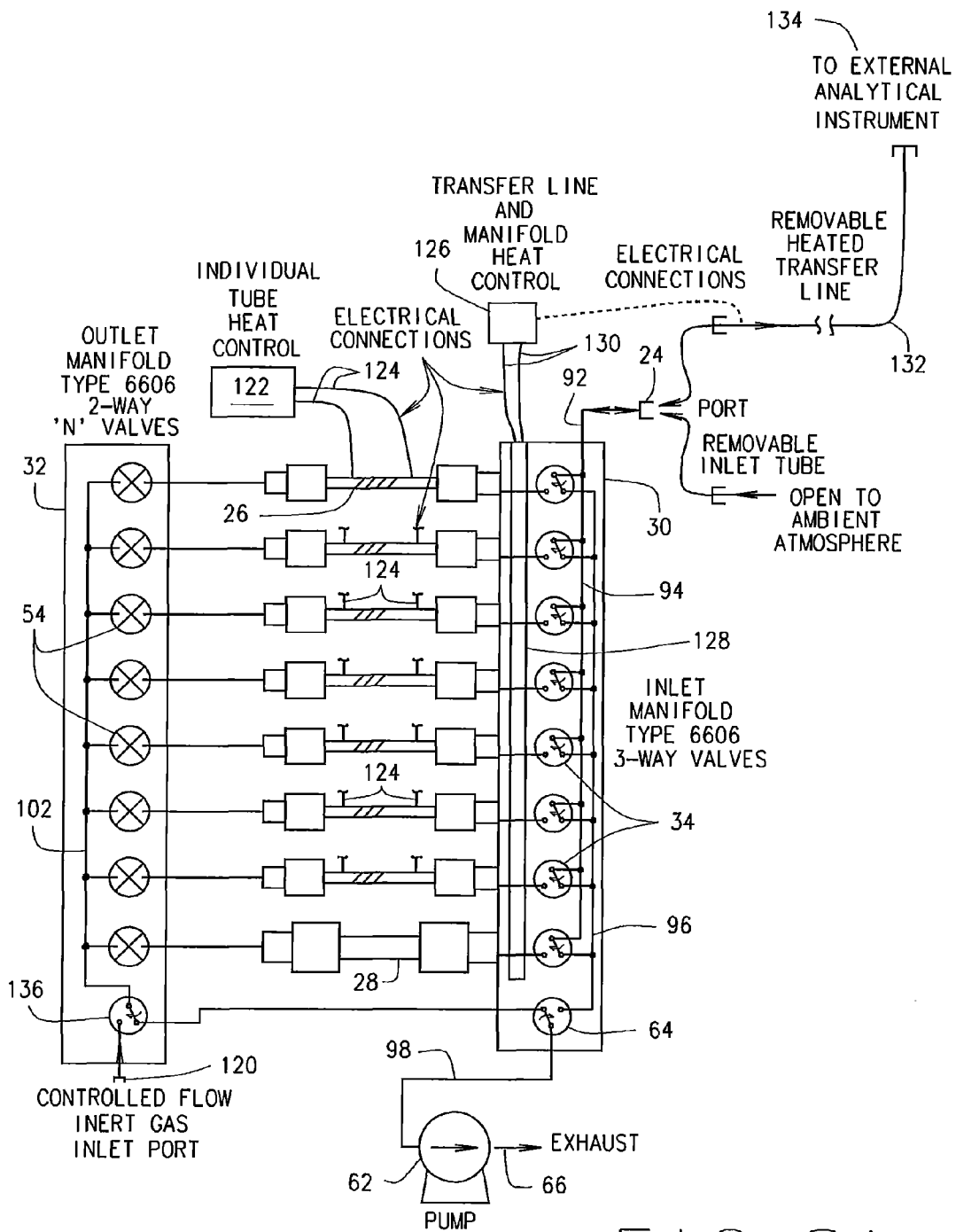
FIG. 8A is a schematic representation illustrating still another embodiment of the present multi-tube air sampler unit illustrating conversion of the present system to a desorbing auto sampler configuration.

FIG. 8A is a schematic representation illustrating still another embodiment of the present device 10 wherein the device 10 can be converted into a desorbing auto-sampler configuration wherein the sample tubes 26 can remain engaged with the inlet and outlet manifolds 30 and 32 and a suitable controlled flow of inert gas can be attached to the inlet port 120 associated with the outlet manifold 32 so as to evacuate the respective tubes 26 in a reverse direction as will be hereinafter further explained. Since the trace elements collected within the respective tubes 26 have been captured by a technique referred to as chemical adsorption, it is typically necessary to heat the respective sample tube and the sorbent material contained therein in order to release the adsorbed trace elements from the sorbent. Once the trace elements are released within the respective tube, it is common practice to carry the sample trace elements within the tube by an inert gas such as pure nitrogen from the tube and from the present device 10 for capture in an external analytical instrument for analyzing such sample. It is also common practice to heat the flow path from the tube 26 or 28 to the external analytical instrument for analysis. Since tube 28 is a type 5 cartridge tube, it is typically removed from the case 12 for analysis purposes. However, if tube 28 is of a different type sorbent tube, tube 28 may also be susceptible to a desorption process for evacuating the trace elements contained therein.

To this end, individual tube heat control means 122 is electrically connected through appropriate connections 124 to each respective tube 26 in a conventional manner. Control means 122 can be selectively programmable or selectively actuatable so as to heat the appropriate selected tube 26 for desorption. In the embodiment illustrated in FIG. 8A, tube 28 is not individually heated since the type 5 cartridge tube is designed for removal from the present device 10 for analysis. It is recognized that this tube station could likewise be heated depending upon the type of sample tube utilized.

In similar fashion, a transfer line and inlet manifold heat control unit 126 is likewise used to provide heat to the inlet manifold 30 and to the various flow paths therethrough through the use of a heater element or other appropriate heater means 128 positioned within the inlet manifold 30. Heat control unit 126 is likewise electrically connected via electrical connections 130 to the heating unit 128 in a conventional manner. Heat control unit 126 is likewise electrically connected to the removable transfer flow path 132 for heating the flow path between an external analytical unit 134 and flow path 92. Here again, the transfer line and inlet manifold heat control unit 126 can be selectively programmed or selectively activated during the desorption process to heat the inlet manifold and its appropriate flow paths including flow path 132 for allowing the desorbed trace elements to be carried by the inert gas through the inlet manifold to the external analytical instrument 134 for analysis purposes.

Once the present device 10 is returned to a remote location for analysis, a source of pure nitrogen is connected to the inlet port 120 associated with the outlet manifold 32. Each tube 26, as it is selected for desorption, is heated via tube heat control means 122 and the inlet manifold 30 and flow path 132 are likewise heated via heat control unit 126. In addition, an external analytical instrument 134 is connected to the external inlet port 24 in place of the external sample probe 18. The sample retrieval and desorption process takes place in the reverse direction as compared to collecting the sample trace elements explained above with respect to FIGS. 6 and 7. Once the trace elements in the selected tube for desorption are heated and released, pure nitrogen is allowed to flow from inlet port 120 through a desorption valve 136 which is moved to its open position as will be hereinafter explained with respect to FIG. 8B to the selected tube 26 for carrying the desorbed trace elements to the external analytical instrument 134.

Figure 8B:
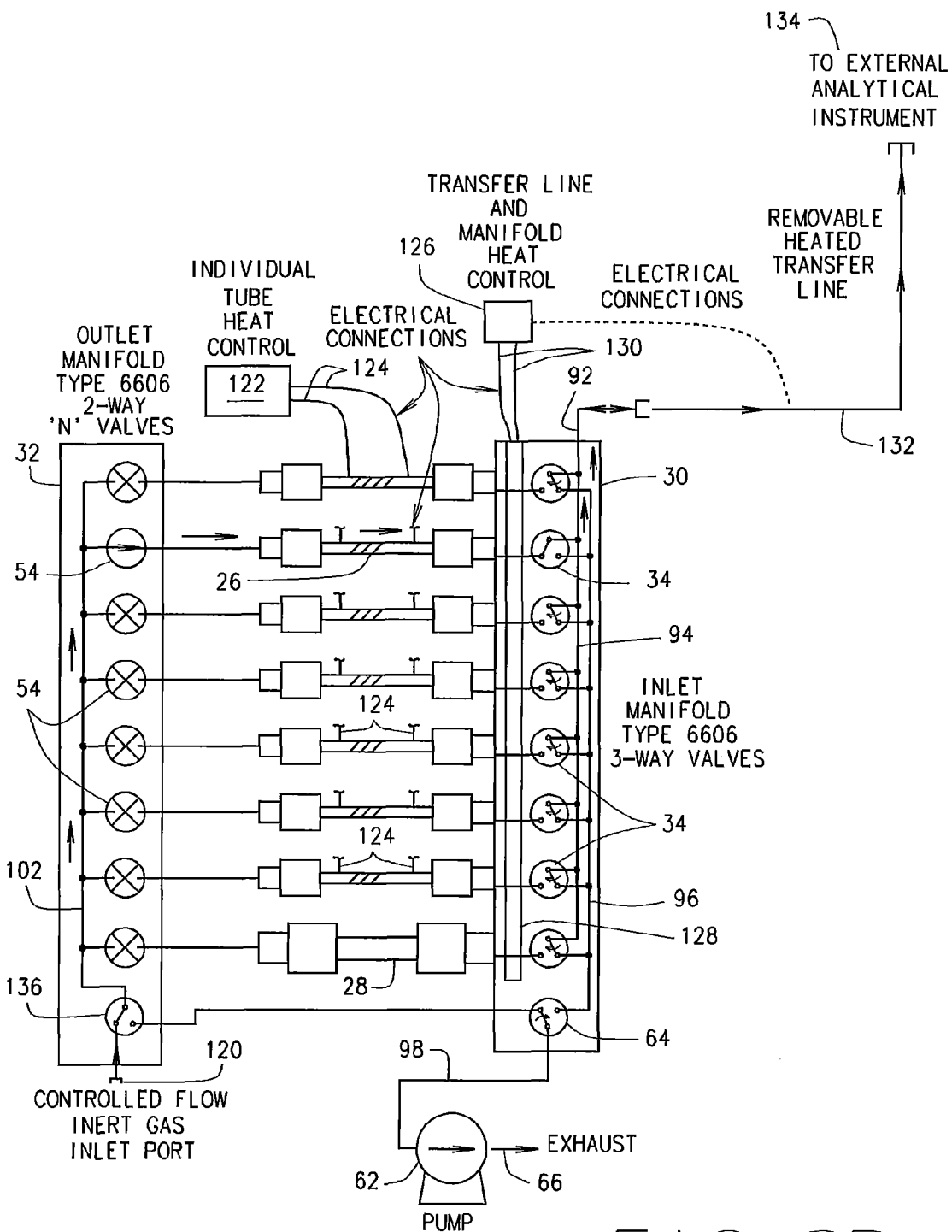
FIG. 8B is a schematic representation similar to FIG. 8A showing the valving arrangement for desorbing a selected sample tube.

FIG. 8B is a schematic representation of the valving arrangement associated with the present device 10 for desorbing a selected sample tube 26. As illustrated in FIG. 8B, once the trace elements in the selected tube 26 are heated and released, the desorption valve 136 is moved to its open position and pure nitrogen is allowed to flow from inlet port 120 through the desorption valve 136 and through outlet manifold 32 along flow path 102 as indicated by the flow direction arrows to the selected tube 26 for desorption. Here again, the electronic control system 72 will select the appropriate tube 26 for desorption and will open the valve 136 and the inlet and outlet valves 34 and 54 associated with that selected tube 26. The nitrogen will then continue to flow at an appropriate flow rate through the appropriate outlet valve 54, through the selected tube 26 for desorption, through the appropriate inlet valve 34, and through the inlet manifold 30 towards the inlet port 24 as illustrated in FIG. 8B. The desorption flow will continue in the opposite direction along flow paths 92 and 132 to the external analytical instrument 134 connected to inlet port 24 for analysis of the collected trace elements. The inlet manifold heat control unit 126 heats the passageway 132 between the inlet port 24 and the analytical instrument 134 so as to again keep the trace elements released within the inert gas carrier as the trace elements are transferred to the analytical instrument 134 for analysis. This reverse flow process can be repeated for each selected tube to be desorbed.

After removing the trace elements from the respective tubes 26 using the heated desorption and carrier gas method described above, the sorbent contained within each tube is typically clean and ready for use in the next sampling sequence. Once the desorption process has been completed, the pure nitrogen source is disconnected from inlet port 120 and the desorption valve 136 is moved to its closed position. The external analytical instrument 134 is likewise removed from the inlet port 24 and the device 10 can be reconfigured for sampling operations as previously described with respect to FIGS. 1-6. Activation of the desorption process can be initiated through the use of conventional means such as through the use of an additional activation switch or button (not shown) associated with the device 10.

In the embodiment illustrated in FIGS. 8A and 8B, it is not necessary to remove the respective sample tube 26 from the device 10 in order to perform the desorption process and to analyze the trace elements. Although cleaning of the respective tube 26 can likewise be accomplished without removing the tubes from the device 10, the respective tubes can be easily removed from the inlet and outlet manifolds as previously explained and can be further cleaned and/or replaced with new cleaned tubes for repeated use if it becomes necessary or advantageous to do so.

As illustrated in FIGS. 8A and 8B, the inlet manifold heat control unit 126 can likewise be utilized to heat the inlet manifold and the sample intake flow path 92 during the sampling process as well in order to prevent contaminant accumulation within the system and carryover from one sampling operation to another. This heating process would take place on each sample cycle and would be in addition to the purging cycle performed prior to each sampling cycle. This heated inlet flow path process further aids in reducing condensation and sample deposition on the manifold walls during the sampling process and helps to keep the sample trace elements from attaching to the inlet manifold thereby increasing the sample component available to be collected within the selected tube. This also reduces contaminant accumulation and carryover between sampling cycles and further aids in purging residual trace elements which may reside in the inlet manifold and inlet flow paths during the sample cycle.

In still another embodiment, a voice recorder can be incorporated into the carrying case 12 and can be activated through the use of another activation switch 138 (FIG. 5) associated with the controller unit 20 during a sampling operation. Use of the voice recorder will allow an operator to audibly collect data and record audible information during the sampling process such as audibly recording the location, sample identification, time of day, and any other appropriate and/or relevant sample information relative to that particular sample cycle. Both the activation button 138 as well as a suitable microphone/speaker 140 can be incorporated into the controller unit 20 as best shown in FIG. 5.

Although the various embodiments disclosed herein have illustrated a plurality of seven tubes 26 and one tube 28, it is recognized and anticipated that the inlet and outlet manifolds 30 and 32 can be configured to accommodate any plurality of tubes 26 and any plurality of tubes 28, or any other appropriate types of sampling sorbent tubes for use with the present device 10. It is likewise recognized and anticipated that the inlet transfer line and inlet manifold heat control unit 126 can be incorporated into the present device 10 separate and apart from the desorption process and separate and apart from tube heat control means 122. Also, although it is preferred that the inlet and outlet manifold assemblies be made of stainless steel, it is recognized that other materials can likewise be utilized depending upon the particular application. In addition, the inlet and outlet manifolds 30 and 32 are placed in parallel on opposing faces of the main system plate 22 so as to minimize the length of the unpurged portion of the sample path between inlet valves 34 on inlet manifold 30 and tubes 26 and 28 as compared to other known devices. This arrangement allows for the sampling tubes to be mounted directly to the inlet manifold yet utilizes tubing 50 for connection to the outlet manifold 32. This not only saves space but it also shortens the operative length of the tubes 26 and 28. In addition, the inlet sample flow paths associated with the inlet manifold 30 are likewise preferably all stainless steel wetted surfaces and are deactivated with a Sulfinert coating (Restek). O-ring type face seal fittings connect the sampling tubes to the inlet manifold 30, and PEEK fittings connect the tubes 50 to the outlet manifold 32. Ports for the heating elements 128 as illustrated in FIGS. 8A and 8B can be easily machined into the inlet manifold 30. In addition, the inlet manifold 30 is also insulated from the main system plate 22 using appropriate spacers.

To minimize particulate contamination, an expendable syringe-style filter can be connected to the inlet port 24 of the case 12 using a Luer-Lock connection. An expendable length of PTFE tubing can likewise be used to connect to the filter and can act as the sampling probe 18. Still further, although 3 way inlet valves 34 and 2 way outlet valves 54 have been described for use with the respective inlet and outlet manifolds, it is recognized and anticipated that any suitable valve can be utilized in association with both the inlet and outlet manifolds so long as the appropriate flow paths are selectively maintained for both the purge cycle and the sampling cycle.

Thus, there has been shown and described several embodiments of a novel portable multi-port air sampler device which is capable of acquiring multiple samples of trace elements in minimum time and with user selectable sampling protocol, which sampler unit fulfills all the objects and advantages sought therefor. Many changes, modifications, variations and other uses and applications of the present invention will, however, become apparent to those skilled in the art after considering this specification and the accompanying drawings. All such drawings, modifications, variations and other uses and applications which do not depart from the spirit and scope of the present invention are deemed to be covered by the present invention which is limited only by the claims which follow.

The invention claimed is:

1. A sampling device for collecting a plurality of separate samples of trace elements from an ambient atmosphere wherein one sample of trace elements is collected per sampling cycle, said sampling device comprising:
   a carrying case;
   an inlet probe for drawing a sample flow of trace elements from an ambient atmosphere to the sampling device during a particular sampling cycle;
   a plurality of removably attachable sample tubes, each sample tube having opposite end portions;
   an inlet manifold having a plurality of inlet valves associated therewith, each inlet valve being associated with a corresponding sample tube;
   an outlet manifold having a plurality of outlet valves associated therewith, each outlet valve being associated with a corresponding sample tube;
   said plurality of sample tubes being operatively connected to said inlet and outlet manifolds and to said corresponding inlet and outlet valves;
   an electronic control system operable for controlling the operation of said inlet and outlet valves for selectively directing a sample flow of trace elements from said inlet probe to one of a selected sample tube during a particular sampling cycle;
   a pump for sequentially drawing a sample flow of trace elements into one of said sample tubes at a time as directed by said electronic control system;
   a removably attachable controller unit operatively connected to said electronic control system, said controller unit being removably attachable to a port located on the exterior of said carrying case for allowing a user to selectively choose any one of a plurality of different sampling protocols; and
   a battery for supplying power to said sampling device.

2. The sampling device defined in claim 1 including a hinged retainer bar assembly for holding one end portion of each of said sample tubes in a fixed position within said carrying case.

3. The sampling device defined in claim 2 wherein said hinged retainer bar assembly includes at least one pivotally movable member, said at least one pivotally movable member being movable between a first closed position wherein the one end portion of at least some of said plurality of sample tubes are held in a fixed position within said carrying case and a second open position wherein the one end portion of at least some of said plurality of sample tubes are free from attachment within said carrying case.

4. The sampling device defined in claim 2 wherein said hinged retainer bar assembly includes first and second pivotally movable members, said first pivotally movable member being movable between a closed position wherein the one end portion of at least some of said plurality of sample tubes are held in a fixed position within said carrying case and an open position wherein the one end portion of at least some of said plurality of sample tubes are no longer held in a fixed position within said carrying case, and wherein said second pivotally movable member is movable between a closed position wherein the one end portion of at least one of said plurality of sample tubes is held in a fixed position within said carrying case and an open position wherein the one end portion of said at least one sample tube is no longer held in a fixed position within said carrying case.

5. The sampling device defined in claim 4 wherein said first and second pivotally movable members include spaced apart cutout portions for respectively engaging the one end portion of said respective sample tubes.

6. The sampling device defined in claim 1 wherein said plurality of sampling protocols includes a sampling cycle of three seconds and a sampling cycle of sixty seconds.

7. The sampling device defined in claim 6 wherein said plurality of sampling protocols further includes a sixty second sampling cycle wherein 1 liter of a sample flow is passed through a type 5 cartridge tube in sixty seconds.

8. The sampling device defined in claim 6 including a pair of indicator lights associated with at least some of said plurality of sample tubes, one indicator light being illuminated when a three second sampling cycle has been used with a respective sample tube, and the other indicator light being illuminated when a sixty second sample cycle has been used with a respective sample tube.

9. The sampling device defined in claim 8 wherein the states of the respective pair of indicator lights are latched for preservation during power down so that upon reapplication of power said indicator lights will again display the current state of each respective tube.

10. The sampling device defined in claim 8 including a reset button positionable within said carrying case, said reset button allowing a user to cancel the illumination of said indicator lights when activated.

11. The sampling device defined in claim 10 wherein activation of said reset button resets said controller unit and said electronic control system for sequentially selecting said sample tubes.

12. The sampling device defined in claim 1 wherein the operation of said sampling device includes a purging cycle, said purging cycle directing a sample flow through the inlet manifold and through the inlet portion of each respective inlet valve for purging any residual trace elements therefrom prior to initiating a particular sampling cycle.

13. The sampling device defined in claim 12 wherein said inlet manifold includes a pump valve, said pump valve being operative for controlling said purging cycle, said pump valve being operatively controlled by said electronic control system.

14. The sampling device defined in claim 12 wherein said electronic control system automatically initiates a purging cycle prior to any sampling cycle when any one of said plurality of sampling protocols are activated through said controller unit.

15. The sampling device defined in claim 12 including a filter positioned upstream from said plurality of inlet valves for purging the incoming sample flow to remove ambient contaminants therefrom, an incoming sample flow being diverted through said filter during a purging cycle.

16. The sampling device defined in claim 1 wherein at least some of said sample tubes are constructed and configured for compatible attachment to a HAPSITE field portable mass spectrometer.

17. The sampling device defined in claim 1 wherein said inlet manifold includes a heating element.

18. The sampling device defined in claim 1 including a plurality of spare sample tubes, said spare sample tubes being housed within said carrying case.

19. The sampling device defined in claim 1 wherein said plurality of sample tubes includes a plurality of tri-bed concentrator tubes and at least one type 5 cartridge tube.

20. The sampling device defined in claim 1 including a voice recorder operable from said control unit for the audible collection of information during a sampling cycle.

21. The sampling device defined in claim 1 wherein said inlet probe is removably attachable to an inlet port located on the exterior portion of said carrying case.

22. The sampling device defined in claim 21 including a sample retrieval and desorption mode for evacuating said sample tubes for analysis wherein said sampling device further includes an inlet port associated with said outlet manifold for attaching an inert gas source thereto, a desorption valve associated with the outlet manifold for controlling the flow of inert gas through the outlet manifold to a selected sample tube for desorption, a heat control unit for individually heating at least some of the sample tubes for desorption, the inlet port of said sampling device being operatively configured to receive an external analytical instrument for receiving the sample of trace elements collected within the selected sample tube for desorption, and a heat control unit for heating the inlet manifold and the flow path between the inlet manifold and an external analytical instrument, said electronic control system controlling said desorption valve and said inlet and outlet valves so as to direct the flow of inert gas from the inlet port of said outlet manifold through a selected sample tube and through said inlet manifold to an external analytical instrument.

23. The sampling device defined in claim 1 including a heat control unit for heating the inlet manifold and the flow path between the inlet probe and the inlet manifold during a sampling cycle.

24. The sampling device defined in claim 1 wherein said controller unit includes an indicator light, said indicator light being illuminated in a steady condition when said sampling device is ready for collecting samples of trace elements, said indicator light being illuminated in a flashing condition during a particular sampling cycle, and said indicator light being unlit when all of said sample tubes have been used.

25. The sampling device defined in claim 1 including a main system plate positionable within said carrying case, said inlet manifold and said sample tubes being positioned on one side of said main system plate and said outlet manifold being positioned in parallel relationship to said inlet manifold on the opposite side of said main system plate.

26. The sampling device defined in claim 1 including a filter positioned upstream from said plurality of inlet valves for purging the incoming sample flow to remove ambient contaminants therefrom, an incoming sample flow being diverted through said filter during a sampling cycle to establish a base line contamination level associated with said sampling device.

27. A sampling device for collecting a plurality of separate samples of trace elements from an ambient atmosphere wherein one sample of trace elements is collected per sampling cycle, said sampling device comprising:
 a portable carrying case;
 an inlet probe for drawing a sample flow of trace elements from an ambient atmosphere to the sampling device during a particular sampling cycle, said inlet probe being removably attachable to an inlet port located on the exterior portion of said carrying case;
 an inlet manifold having a plurality of inlet valves associated therewith;
 an outlet manifold having a plurality of outlet valves associated therewith;
 a plurality of sample tubes operatively connected to said inlet and outlet manifolds and to said corresponding inlet and outlet valves;
 an electronic control system operable for controlling the operation of said inlet and outlet valves for selectively directing a sample flow of trace elements from said inlet probe to one of a selected sample tube during a particular sampling cycle;

a pump for sequentially drawing a sample flow of trace elements into one of said sample tubes at a time as directed by said electronic control system;

a battery for supplying power to said sampling device; and said electronic control system being further operable to control and to automatically initiate a purging cycle prior to any sampling cycle, said purging cycle directing a sample flow through the inlet manifold and through the inlet portion of each respective inlet valve for purging any residual trace elements therefrom prior to initiating a particular sampling cycle.

28. The sampling device defined in claim 27 wherein said electronic control system includes a controller unit, said controller unit being removably attachable to said electronic control system through a port located on the exterior of said carrying case, said controller unit allowing a user to selectively choose any one of a plurality of different sampling protocols.

29. The sampling device defined in claim 28 wherein said plurality of sampling protocols includes a sampling cycle of three seconds and a sampling cycle of sixty seconds.

30. The sampling device defined in claim 27 including at least one pivotally rotatable retainer bar member for holding one end portion of each of said sample tubes in a fixed position within said carrying case, said at least one pivotally rotatable retainer bar member being movable between a closed position wherein the one end portion of each of said sample tubes is held in a fixed position within said carrying case and an open position wherein the one end portion of each of said sample tubes is no longer held in a fixed position within said carrying case.

31. The sampling device defined in claim 27 wherein said inlet manifold includes a pump valve, said pump valve being operative for controlling said purging cycle and said sampling cycles, said pump valve being operatively controlled by said electronic control system.

32. The sampling device defined in claim 27 including a filter positioned upstream from said plurality of inlet valves, an incoming sample flow being diverted through said filter during a purging cycle to remove ambient contaminants therefrom.

33. A sampling device for collecting samples of trace elements from an ambient atmosphere comprising:

a portable carrying case;

an inlet probe for drawing a sample flow of trace elements from an ambient atmosphere to the sampling device;

an inlet manifold having a plurality of inlet valves associated therewith;

an outlet manifold having a plurality of outlet valves associated therewith;

a plurality of sample tubes each having opposite end portions, one end portion of each of said sample tubes being attachable to said inlet manifold and to a corresponding inlet valve, the opposite end portion of each of said sample tubes being fixedly retained within a hinged retainer bar assembly, said hinged retainer bar assembly being movable between a closed position wherein the opposite end portion of each of said sample tubes is held in a fixed position and an open position wherein the opposite end portion of each of said sample tubes is no longer held in a fixed position, the opposite end portion of each of said sample tubes being operatively connected to said outlet manifold;

an electronic control system for controlling the operation of said inlet and outlet valves for selectively directing a sample flow of trace elements from said inlet probe to one of a selected sample tube;

a pump for sequentially drawing a sample flow of trace elements into one of said sample tubes at a time as directed by said electronic control system; and a battery for supplying power to said sampling device.

34. The sampling device defined in claim 33 wherein said hinge retainer bar assembly includes first and second pivotally movable members, said first pivotally movable member being movable between a closed position wherein the opposite end portion of at least some of said plurality of sample tubes are held in a fixed position and an open position wherein the opposite end portion of at least some of said plurality of sample tubes are no longer held in a fixed position, and wherein said second pivotally movable member is movable between a closed position wherein the opposite end portion of at least one of said plurality of sample tubes is held in a fixed position and an open position wherein the opposite end portion of said at least one sample tube is no longer held in a fixed position.

35. The sampling device defined in claim 33 including a removably attachable controller unit operatively connected to said electronic control system, said controller unit being removably attachable to a port located on the exterior of said carrying case for allowing a user to selectively choose any one of a plurality of different sampling protocols.

36. The sampling device defined in claim 35 wherein said plurality of sampling protocols includes a sampling cycle of three seconds and a sampling cycle of sixty seconds.

37. The sampling device defined in claim 33 wherein the operation of said sampling device includes a purging cycle, said purging cycle directing a sample flow through the inlet manifold and through the inlet portion of each respective inlet valve for purging any residual trace elements therefrom prior to initiating a sampling cycle.

38. The sampling device defined in claim 37 wherein said electronic control system automatically initiates a purging cycle prior to any sampling cycle.

39. The sampling device defined in claim 38 including a filter positioned upstream from said plurality of inlet valves, an incoming sample flow being diverted through said filter during a purging cycle for purging the incoming sample flow to remove ambient contaminants therefrom.

40. The sampling device defined in claim 33 including a sample retrieval and desorption mode for evacuating said sample tubes for analysis wherein said sampling device further includes an inlet port associated with said outlet manifold for attaching an inert gas source thereto, a desorption valve associated with the outlet manifold for controlling the flow of inert gas through the outlet manifold to a selected sample tube for desorption, a heat control unit for individually heating at least some of the sample tubes for desorption, the inlet port of said sampling device being operatively configured to receive an external analytical instrument for receiving the sample of trace elements collected within the selected sample tube for desorption, and a heat control unit for heating the inlet manifold and the flow path between the inlet manifold and an external analytical instrument, said electronic control system controlling said desorption valve and said inlet and outlet valves so as to direct the flow of inert gas from the inlet port of said outlet manifold through a selected sample tube and through said inlet manifold to an external analytical instrument.

41. A sampling device for collecting a plurality of samples of trace elements from an ambient atmosphere during a plurality of sampling cycles, each sampling cycle collecting one sample of trace elements, said sampling device comprising:

a portable carrying case;

a removably attachable inlet probe for drawing a sample flow of trace elements from an ambient atmosphere to the sampling device during a particular sampling cycle, said inlet probe being removably attachable to an inlet port located on the exterior portion of said carrying case;

a plurality of removably attachable sample tubes, each sample tube having opposite end portions;

an inlet manifold having a plurality of inlet valves associated therewith, each inlet valve being associated with the corresponding sample tubes;

an outlet manifold having a plurality of outlet valves associated therewith, each outlet valve being associated with the corresponding sample tubes;

said plurality of sample tubes having one end portion fixedly connected to said inlet manifold and to said corresponding inlet valves and having their opposite end portions operatively connected to said outlet manifold and to said corresponding outlet valves;

a hinged retainer bar member for holding the opposite end portion of each of said sample tubes in a fixed position within said carrying case, said hinged retainer bar member including first and second pivotally movable members, said first pivotally movable member being movable between a closed position wherein the opposite end portion of at least some of said plurality of sample tubes are held in a fixed position within said carrying case and an open position wherein the opposite end portion of at least some of said plurality of sample tubes are free from attachment within said carrying case, and wherein said second pivotally movable member is movable between a closed position wherein the opposite end portion of at least one of said plurality of sample tubes is held in a fixed position within said carrying case and an open position wherein the opposite end portion of said at least one sample tube is free from attachment within said carrying case;

an electronic control system operable for controlling the operation of said inlet and outlet valves for selectively directing a sample flow of trace elements from said inlet probe to one of a selected sample tube during a particular sampling cycle;

a pump for sequentially drawing a sample flow of trace elements into one of said sample tubes at a time as directed by said electronic control system;

a controller unit operatively connected to said electronic control system, said controller unit being removably attachable to a port located on the exterior of said carrying case for allowing a user to selectively choose any one of a plurality of different sampling protocols; and a battery for supplying power to said sampling device.

42. The sampling device defined in claim 41 wherein said plurality of sampling protocols includes a sampling cycle of three seconds and a sampling cycle of sixty seconds.

43. The sampling device defined in claim 42 wherein said plurality of sampling protocols further includes a sixty second sampling cycle wherein one liter of a sample flow is passed through a type 5 cartridge tube in sixty seconds.

44. The sampling device defined in claim 42 including a pair of indicator lights associated with at least some of said plurality of sample tubes, one indicator light being illuminated when a three second sampling cycle has been used with a respective sample tube, and the other indicator light being illuminated when a sixty second sample cycle has been used with a respective sample tube.

45. The sampling device defined in claim 41 wherein the operation of said sampling device includes a purging cycle, said purging cycle directing a sample flow through the inlet manifold and through the inlet portion of each respective inlet valve for purging any residual trace elements therefrom prior to initiating a particular sampling cycle.

46. The sampling device defined in claim 44 wherein said electronic control system automatically initiates a purging cycle prior to any sampling cycle when any one of said plurality of sampling protocols are activated through said controller unit.

47. The sampling device defined in claim 41 wherein said plurality of sample tubes includes a plurality of tri-bed concentrator tubes and at least one type 5 cartridge tube.

48. The sampling device defined in claim 41 including a sample retrieval and desorption mode for evacuating said sample tubes for analysis wherein said sampling device further includes an inlet port associated with said outlet manifold for attaching an inert gas source thereto, a desorption valve associated with the outlet manifold for controlling the flow of inert gas through the outlet manifold to a selected sample tube for desorption, a heat control unit for individually heating at least some of the sample tubes for desorption, the inlet port of said sampling device being operatively configured to receive an external analytical instrument for receiving the sample of trace elements collected within the selected sample tube for desorption, and a heat control unit for heating the inlet manifold and the flow path between the inlet manifold and an external analytical instrument, said electronic control system controlling said desorption valve and said inlet and outlet valves so as to direct the flow of inert gas from the inlet port of said outlet manifold through a selected sample tube and through said inlet manifold to an external analytical instrument.

49. The sampling device defined in claim 41 wherein said controller unit includes an indicator light, said indicator light being illuminated in a steady condition when said sampling device is ready for collecting samples of trace elements, said indicator light being illuminated in a flashing condition during a particular sampling cycle, and said indicator light being unlit when all of said sample tubes have been used.

50. The sampling device defined in claim 41 wherein said first and second pivotally movable members include spaced apart cutout portions for respectively engaging the one end portion of said respective sample tubes.

* * * * *